(12) United States Patent
Kim et al.

(10) Patent No.: US 10,407,475 B2
(45) Date of Patent: Sep. 10, 2019

(54) PROTEIN SECRETORY FACTOR WITH HIGH SECRETORY EFFICIENCY AND AN EXPRESSION VECTOR COMPRISING THE SAME

(71) Applicant: LG CHEM, LTD., Seoul (KR)

(72) Inventors: Seung Hae Kim, Seoul (KR); Yeon Chul Kim, Seoul (KR); Saem Jung, Seoul (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/307,322

(22) PCT Filed: Apr. 30, 2015

(86) PCT No.: PCT/KR2015/004389
§ 371 (c)(1),
(2) Date: Oct. 27, 2016

(87) PCT Pub. No.: WO2015/167278
PCT Pub. Date: Nov. 5, 2015

(65) Prior Publication Data
US 2017/0044224 A1    Feb. 16, 2017

(30) Foreign Application Priority Data
Apr. 30, 2014   (KR) .................. 10-2014-0052752

(51) Int. Cl.
| | |
|---|---|
| C07K 14/47 | (2006.01) |
| C07K 14/82 | (2006.01) |
| C07K 16/00 | (2006.01) |
| C12N 15/85 | (2006.01) |
| C12P 21/02 | (2006.01) |

(52) U.S. Cl.
CPC ............. *C07K 14/47* (2013.01); *C07K 14/82* (2013.01); *C07K 16/00* (2013.01); *C12N 15/85* (2013.01); *C12P 21/02* (2013.01); *C07K 2317/51* (2013.01); *C07K 2317/515* (2013.01); *C07K 2319/00* (2013.01); *C07K 2319/02* (2013.01)

(58) Field of Classification Search
None
See application file for complete search history.

(56) References Cited

U.S. PATENT DOCUMENTS

| | | | | |
|---|---|---|---|---|
| 6,022,847 | A * | 2/2000 | Sheppard ............... | C07K 14/47 424/1.69 |
| 6,312,922 | B1 | 11/2001 | Edwards et al. | |
| 6,365,369 | B1 | 4/2002 | Endress et al. | |
| 7,317,091 | B2 * | 1/2008 | Lazar .................... | C07K 16/00 530/387.1 |
| 8,278,412 | B2 | 10/2012 | Zheng | |
| 2003/0059885 | A1 | 3/2003 | Baker et al. | |
| 2012/0082667 | A1 * | 4/2012 | Yokoseki ............... | C07K 16/18 424/133.1 |

FOREIGN PATENT DOCUMENTS

| | | |
|---|---|---|
| EP | 1666497 A2 | 6/2006 |
| JP | 2007-209328 A | 8/2007 |
| KR | 10-2003-0062854 A | 7/2003 |
| KR | 10-2007-0119250 A | 12/2007 |
| KR | 10-0954322 B1 | 4/2010 |
| KR | 10-2012-0059222 A | 6/2012 |
| WO | WO 2007/145466 A1 | 12/2007 |
| WO | WO 2013/151668 A2 | 10/2013 |
| WO | WO 2014/058389 A1 | 4/2014 |

OTHER PUBLICATIONS

Kober et al., Biotechnol. Bioeng. 2013;110(4): 1164-1173.*
NCBI, "Zymogen granule protein 16 homolog B precursor," NCBI Reference Sequence: NP_660295.2, accessed at http://www.ncbi.nlm.nih.gov/protein/94536866?sat=18&satkey=1506228, accessed on Jul. 13, 2015.
International Search Report and Written Opinion for International Application No. PCT/KR2015/004389, Korean Intellectual Property Office, dated Jul. 23, 2015, 12 pages.
Extended European Search Report for European Application No. 15785585.9, European Patent Office, dated Oct. 16, 2017, 7 pages.

* cited by examiner

*Primary Examiner* — Marianne P Allen
(74) *Attorney, Agent, or Firm* — Rothwell, Figg, Ernst & Manbeck, P.C.

(57) ABSTRACT

The present invention relates to a novel protein secretion factor, a vector including a nucleic acid sequence encoding the protein secretion factor, and a transformed cell into which the vector is introduced. The invention also relates to a method of producing a target protein using the transformed cell including the vector.

14 Claims, 12 Drawing Sheets

Specification includes a Sequence Listing.

SEQUENCE LISTING

```
<160> NUMBER OF SEQ ID NOS: 50

<210> SEQ ID NO 1
<211> LENGTH: 22
<212> TYPE: PRT
<213> ORGANISM: Artificial Sequence
<220> FEATURE:
<223> OTHER INFORMATION: signal peptide_SP7.2

<400> SEQUENCE: 1

Met His Arg Pro Glu Ala Met Leu Leu Leu Leu Thr Leu Ala Leu Leu
1               5                   10                  15

Gly Gly Pro Thr Trp Ala
```

<210> SEQ ID NO 2
<211> LENGTH: 40
<212> TYPE: PRT
<213> ORGANISM: Artificial Sequence
<220> FEATURE:
<223> OTHER INFORMATION: signal peptide_SP7.3

<400> SEQUENCE: 2

Met Trp Arg Val Pro Gly Thr Thr Arg Arg Pro Val Thr Gly Glu Ser
1               5                   10                  15

Pro Gly Met His Arg Pro Glu Ala Met Leu Leu Leu Thr Leu Ala
            20                  25                  30

Leu Leu Gly Gly Pro Thr Trp Ala
        35                  40

<210> SEQ ID NO 3
<211> LENGTH: 19
<212> TYPE: PRT
<213> ORGANISM: Artificial Sequence
<220> FEATURE:
<223> OTHER INFORMATION: signal peptide_SP1

<400> SEQUENCE: 3

Met Gly Trp Ser Tyr Ile Ile Leu Phe Leu Val Ala Thr Ala Thr Asp
1               5                   10                  15

Val His Ser

<210> SEQ ID NO 4
<211> LENGTH: 24
<212> TYPE: PRT
<213> ORGANISM: Artificial Sequence
<220> FEATURE:
<223> OTHER INFORMATION: signal peptide_SP2

<400> SEQUENCE: 4

Met Lys Trp Val Thr Phe Ile Ser Leu Leu Phe Leu Phe Ser Ser Ala
1               5                   10                  15

Tyr Ser Arg Gly Val Phe Arg Arg
            20

<210> SEQ ID NO 5
<211> LENGTH: 22
<212> TYPE: PRT
<213> ORGANISM: Artificial Sequence
<220> FEATURE:
<223> OTHER INFORMATION: signal peptide_SP3

<400> SEQUENCE: 5

Met Asp Phe Gln Val Gln Ile Ile Ser Phe Leu Leu Ile Ser Ala Ser
1               5                   10                  15

Val Ile Met Ser Arg Gly
            20

<210> SEQ ID NO 6
<211> LENGTH: 19
<212> TYPE: PRT
<213> ORGANISM: Artificial Sequence
<220> FEATURE:
<223> OTHER INFORMATION: signal peptide_SP4

<400> SEQUENCE: 6

Met Gly Trp Ser Leu Ile Leu Leu Phe Leu Val Ala Val Ala Thr Arg

Val Leu Ser

<210> SEQ ID NO 7
<211> LENGTH: 17
<212> TYPE: PRT
<213> ORGANISM: Artificial Sequence
<220> FEATURE:
<223> OTHER INFORMATION: signal peptide_SP5

<400> SEQUENCE: 7

Met Leu Leu Leu Leu Leu Leu Leu Gly Leu Arg Leu Gln Leu Ser Leu
1               5                   10                  15

Gly

<210> SEQ ID NO 8
<211> LENGTH: 18
<212> TYPE: PRT
<213> ORGANISM: Artificial Sequence
<220> FEATURE:
<223> OTHER INFORMATION: signal peptide_SP6

<400> SEQUENCE: 8

Met Lys Thr Leu Ile Leu Ala Val Ala Leu Val Tyr Cys Ala Thr Val
1               5                   10                  15

His Cys

<210> SEQ ID NO 9
<211> LENGTH: 29
<212> TYPE: DNA
<213> ORGANISM: Artificial Sequence
<220> FEATURE:
<223> OTHER INFORMATION: oSP1-f primer

<400> SEQUENCE: 9
ttggatccgc caccatggga tggagctat                                 29

<210> SEQ ID NO 10
<211> LENGTH: 33
<212> TYPE: DNA
<213> ORGANISM: Artificial Sequence
<220> FEATURE:
<223> OTHER INFORMATION: oSP1-r primer

<400> SEQUENCE: 10
ttcatatgga cagtcctggg agtggacatc tgt                            33

<210> SEQ ID NO 11
<211> LENGTH: 25
<212> TYPE: DNA
<213> ORGANISM: Artificial Sequence
<220> FEATURE:
<223> OTHER INFORMATION: oCLUC-N1-f primer

<400> SEQUENCE: 11
ttccatatga acctgatcca ccaaa                                     25

<210> SEQ ID NO 12
<211> LENGTH: 25
<212> TYPE: DNA
<213> ORGANISM: Artificial Sequence
<220> FEATURE:
<223> OTHER INFORMATION: oBasic-r primer

<400> SEQUENCE: 12

```
tcagaagcca tagagcccac cgcat                                          25

<210> SEQ ID NO 13
<211> LENGTH: 72
<212> TYPE: DNA
<213> ORGANISM: Artificial Sequence
<220> FEATURE:
<223> OTHER INFORMATION: oHSAL-U primer

<400> SEQUENCE: 13
atgaagtggg tgaccttcat ctccctgctg ttcctgttct cctccgccta ctccaggggc    60
gtgttcagga gg                                                        72

<210> SEQ ID NO 14
<211> LENGTH: 50
<212> TYPE: DNA
<213> ORGANISM: Artificial Sequence
<220> FEATURE:
<223> OTHER INFORMATION: oHSAL-L primer

<400> SEQUENCE: 14
cctcctgaac acgcccctgg agtaggcgga ggagaacagg aacagcaggg               50

<210> SEQ ID NO 15
<211> LENGTH: 29
<212> TYPE: DNA
<213> ORGANISM: Artificial Sequence
<220> FEATURE:
<223> OTHER INFORMATION: oSP2-f primer

<400> SEQUENCE: 15
ttggatccgc caccatgaag tgggtgacc                                      29

<210> SEQ ID NO 16
<211> LENGTH: 33
<212> TYPE: DNA
<213> ORGANISM: Artificial Sequence
<220> FEATURE:
<223> OTHER INFORMATION: oSP2-r primer

<400> SEQUENCE: 16
ttcatatgga cagtcctgcc tcctgaacac gcc                                 33

<210> SEQ ID NO 17
<211> LENGTH: 29
<212> TYPE: DNA
<213> ORGANISM: Artificial Sequence
<220> FEATURE:
<223> OTHER INFORMATION: oSP3-f primer

<400> SEQUENCE: 17
ttggatccgc caccatggac ttccaggtg                                      29

<210> SEQ ID NO 18
<211> LENGTH: 33
<212> TYPE: DNA
<213> ORGANISM: Artificial Sequence
<220> FEATURE:
<223> OTHER INFORMATION: oSP3-r primer

<400> SEQUENCE: 18
ttcatatgga cagtcctggc ccctggacat gat                                 33

<210> SEQ ID NO 19
```

```
<211> LENGTH: 29
<212> TYPE: DNA
<213> ORGANISM: Artificial Sequence
<220> FEATURE:
<223> OTHER INFORMATION: oSP4-f primer

<400> SEQUENCE: 19
ttggatccgc caccatgggc tggagcctg                                      29

<210> SEQ ID NO 20
<211> LENGTH: 33
<212> TYPE: DNA
<213> ORGANISM: Artificial Sequence
<220> FEATURE:
<223> OTHER INFORMATION: oSP4-r primer

<400> SEQUENCE: 20
ttcatatgga cagtcctggg acagcaccct ggt                                 33

<210> SEQ ID NO 21
<211> LENGTH: 39
<212> TYPE: DNA
<213> ORGANISM: Artificial Sequence
<220> FEATURE:
<223> OTHER INFORMATION: oSP5-f primer

<400> SEQUENCE: 21
ttggatccgc caccatgctg ctgctgctgc tgctgctgg                           39

<210> SEQ ID NO 22
<211> LENGTH: 33
<212> TYPE: DNA
<213> ORGANISM: Artificial Sequence
<220> FEATURE:
<223> OTHER INFORMATION: oSP5-r primer

<400> SEQUENCE: 22
ttcatatgga cagtcctggc ccagggagag ctg                                 33

<210> SEQ ID NO 23
<211> LENGTH: 29
<212> TYPE: DNA
<213> ORGANISM: Artificial Sequence
<220> FEATURE:
<223> OTHER INFORMATION: oSP7-B1-f2 primer

<400> SEQUENCE: 23
ttggatccgc caccatgcac cggccagag                                      29

<210> SEQ ID NO 24
<211> LENGTH: 33
<212> TYPE: DNA
<213> ORGANISM: Artificial Sequence
<220> FEATURE:
<223> OTHER INFORMATION: oSP7-N1-r primer

<400> SEQUENCE: 24
ttcatatgga cagtcctgtg cccaggtggg gcc                                 33

<210> SEQ ID NO 25
<211> LENGTH: 29
<212> TYPE: DNA
<213> ORGANISM: Artificial Sequence
<220> FEATURE:
<223> OTHER INFORMATION: oSP7-B1-f3 primer

<400> SEQUENCE: 25
```
ttggatccgc caccatgtgg agggtgccc                                   29

<210> SEQ ID NO 26
<211> LENGTH: 30
<212> TYPE: DNA
<213> ORGANISM: Artificial Sequence
<220> FEATURE:
<223> OTHER INFORMATION: oIxLs-r1 primer

<400> SEQUENCE: 26
cagcaggatg tcgcccctgg acatgatcac                                  30

<210> SEQ ID NO 27
<211> LENGTH: 21
<212> TYPE: DNA
<213> ORGANISM: Artificial Sequence
<220> FEATURE:
<223> OTHER INFORMATION: oRx-LF1 primer

<400> SEQUENCE: 27
cagatcgtgc tgtctcagtc t                                           21

<210> SEQ ID NO 28
<211> LENGTH: 27
<212> TYPE: DNA
<213> ORGANISM: Artificial Sequence
<220> FEATURE:
<223> OTHER INFORMATION: oIkC-M1X1-r primer

<400> SEQUENCE: 28
ttacgcgtct cgagtcaaca ctctccc                                     27

<210> SEQ ID NO 29
<211> LENGTH: 25
<212> TYPE: DNA
<213> ORGANISM: Artificial Sequence
<220> FEATURE:
<223> OTHER INFORMATION: oRHn-f primer

<400> SEQUENCE: 29
ttggcgcgcc atgggatgga gctat                                       25

<210> SEQ ID NO 30
<211> LENGTH: 36
<212> TYPE: DNA
<213> ORGANISM: Artificial Sequence
<220> FEATURE:
<223> OTHER INFORMATION: oIxLs-r2 primer

<400> SEQUENCE: 30
cagcaggatg tcggacagca ccctggtggc cacggc                           36

<210> SEQ ID NO 31
<211> LENGTH: 20
<212> TYPE: DNA
<213> ORGANISM: Artificial Sequence
<220> FEATURE:
<223> OTHER INFORMATION: oRx_HF1 primer

<400> SEQUENCE: 31
caggtgcagc tgcagcagcc                                             20

<210> SEQ ID NO 32
<211> LENGTH: 32
<212> TYPE: DNA

```
<213> ORGANISM: Artificial Sequence
<220> FEATURE:
<223> OTHER INFORMATION: oIgG1-X1N1-r primer

<400> SEQUENCE: 32
aactcgaggc ggccgctcat ttacccggag ac                              32

<210> SEQ ID NO 33
<211> LENGTH: 25
<212> TYPE: DNA
<213> ORGANISM: Artificial Sequence
<220> FEATURE:
<223> OTHER INFORMATION: oAscI_SP2-f primer

<400> SEQUENCE: 33
ctggcgcgcc atgaagtggg tgacc                                      25

<210> SEQ ID NO 34
<211> LENGTH: 25
<212> TYPE: DNA
<213> ORGANISM: Artificial Sequence
<220> FEATURE:
<223> OTHER INFORMATION: oSP2_RH-r primer

<400> SEQUENCE: 34
gcagctgcac ctgcctcctg aacac                                      25

<210> SEQ ID NO 35
<211> LENGTH: 25
<212> TYPE: DNA
<213> ORGANISM: Artificial Sequence
<220> FEATURE:
<223> OTHER INFORMATION: oSP2_RH-f primer

<400> SEQUENCE: 35
gtgttcagga ggcaggtgca gctgc                                      25

<210> SEQ ID NO 36
<211> LENGTH: 26
<212> TYPE: DNA
<213> ORGANISM: Artificial Sequence
<220> FEATURE:
<223> OTHER INFORMATION: oAscI_SP6-f primer

<400> SEQUENCE: 36
caggcgcgcc atgaagacct taattc                                     26

<210> SEQ ID NO 37
<211> LENGTH: 24
<212> TYPE: DNA
<213> ORGANISM: Artificial Sequence
<220> FEATURE:
<223> OTHER INFORMATION: oSP6_RH-r primer

<400> SEQUENCE: 37
gcagctgcac ctggcaatga acag                                       24

<210> SEQ ID NO 38
<211> LENGTH: 24
<212> TYPE: DNA
<213> ORGANISM: Artificial Sequence
<220> FEATURE:
<223> OTHER INFORMATION: oSP6_RH-f primer

<400> SEQUENCE: 38
ctgttcattg ccaggtgcag ctgc                                       24
```

<210> SEQ ID NO 39
<211> LENGTH: 25
<212> TYPE: DNA
<213> ORGANISM: Artificial Sequence
<220> FEATURE:
<223> OTHER INFORMATION: oAscI_SP7.2-f primer

<400> SEQUENCE: 39
caggcgcgcc atgcaccggc cagag                                            25

<210> SEQ ID NO 40
<211> LENGTH: 25
<212> TYPE: DNA
<213> ORGANISM: Artificial Sequence
<220> FEATURE:
<223> OTHER INFORMATION: oSP7.2_RH-r primer

<400> SEQUENCE: 40
gcagctgcac ctgtgcccag gtggg                                            25

<210> SEQ ID NO 41
<211> LENGTH: 25
<212> TYPE: DNA
<213> ORGANISM: Artificial Sequence
<220> FEATURE:
<223> OTHER INFORMATION: oSP7.2_RH-f primer

<400> SEQUENCE: 41
cccacctggg cacaggtgca gctgc                                            25

<210> SEQ ID NO 42
<211> LENGTH: 25
<212> TYPE: DNA
<213> ORGANISM: Artificial Sequence
<220> FEATURE:
<223> OTHER INFORMATION: oSP2_RL-r primer

<400> SEQUENCE: 42
acagcacgat ctgcctcctg aacac                                            25

<210> SEQ ID NO 43
<211> LENGTH: 25
<212> TYPE: DNA
<213> ORGANISM: Artificial Sequence
<220> FEATURE:
<223> OTHER INFORMATION: oSP2_RL-f primer

<400> SEQUENCE: 43
gtgttcagga ggcagatcgt gctgt                                            25

<210> SEQ ID NO 44
<211> LENGTH: 29
<212> TYPE: DNA
<213> ORGANISM: Artificial Sequence
<220> FEATURE:
<223> OTHER INFORMATION: oSP6-f primer

<400> SEQUENCE: 44
ttggatccgc caccatgaag accttaatt                                        29

<210> SEQ ID NO 45
<211> LENGTH: 24
<212> TYPE: DNA
<213> ORGANISM: Artificial Sequence
<220> FEATURE:

<223> OTHER INFORMATION: oSP6_RL-r primer

<400> SEQUENCE: 45
acagcacgat ctggcaatga acag    24

<210> SEQ ID NO 46
<211> LENGTH: 24
<212> TYPE: DNA
<213> ORGANISM: Artificial Sequence
<220> FEATURE:
<223> OTHER INFORMATION: oSP6_RL-f primer

<400> SEQUENCE: 46
ctgttcattg ccagatcgtg ctgt    24

<210> SEQ ID NO 47
<211> LENGTH: 196
<212> TYPE: DNA
<213> ORGANISM: Artificial Sequence
<220> FEATURE:
<223> OTHER INFORMATION: cDNA sequence of human gene LBFL313
<220> FEATURE:
<221> NAME/KEY: CDS
<222> LOCATION: (53)..(196)
<223> OTHER INFORMATION: human LBFL313 cDNA, translation product at SEQ
      ID 50

<400> SEQUENCE: 47
cgcttcttcc ttctggatgg gggcccaggg ggcccaggag agtataaagg cg atg tgg    58
                                                         Met Trp
                                                          1 agg gtg ccc ggc aca acc aga cgc cca gtc aca ggc gag agc cct ggg    106
Arg Val Pro Gly Thr Thr Arg Arg Pro Val Thr Gly Glu Ser Pro Gly
     5                  10                  15 atg cac cgg cca gag gcc atg ctg ctg ctc acg ctt gcc ctc ctg       154
Met His Arg Pro Glu Ala Met Leu Leu Leu Thr Leu Ala Leu Leu
 20                  25                  30 ggg ggc ccc acc tgg gca ggg aag atg tat ggc cct gga gga          196
Gly Gly Pro Thr Trp Ala Gly Lys Met Tyr Gly Pro Gly Gly
 35                  40                  45

<210> SEQ ID NO 48
<211> LENGTH: 213
<212> TYPE: PRT
<213> ORGANISM: Artificial Sequence
<220> FEATURE:
<223> OTHER INFORMATION: Rx antibody light chain a.a.

<400> SEQUENCE: 48

Gln Ile Val Leu Ser Gln Ser Pro Ala Ile Leu Ser Ala Ser Pro Gly
 1               5                  10                  15

Glu Lys Val Thr Met Thr Cys Arg Ala Ser Ser Ser Val Ser Tyr Ile
             20                  25                  30

His Trp Phe Gln Gln Lys Pro Gly Ser Ser Pro Lys Pro Trp Ile Tyr
         35                  40                  45

Ala Thr Ser Asn Leu Ala Ser Gly Val Pro Val Arg Phe Ser Gly Ser
     50                  55                  60

Gly Ser Gly Thr Ser Tyr Ser Leu Thr Ile Ser Arg Val Glu Ala Glu
 65                  70                  75                  80

Asp Ala Ala Thr Tyr Tyr Cys Gln Gln Trp Thr Ser Asn Pro Pro Thr
                 85                  90                  95

Phe Gly Gly Gly Thr Lys Leu Glu Ile Lys Arg Thr Val Ala Ala Pro
            100                 105                 110

```
Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 49
<211> LENGTH: 451
<212> TYPE: PRT
<213> ORGANISM: Artificial Sequence
<220> FEATURE:
<223> OTHER INFORMATION: Rx antibody heavy chain a.a.

<400> SEQUENCE: 49

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Ala Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255
```

```
Ile Ser Arg Thr Pro Glu Val Thr Cys Val Val Asp Val Ser His
            260                 265                 270
Glu Asp Pro Glu Val Lys Phe Asn Trp Tyr Val Asp Gly Val Glu Val
            275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
            355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
                420                 425                 430
His Glu Ala Leu His Asn His Tyr Thr Gln Lys Ser Leu Ser Leu Ser
            435                 440                 445
Pro Gly Lys
    450

<210> SEQ ID NO 50
<211> LENGTH: 48
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(48)
<223> OTHER INFORMATION: translation product of SEQ ID NO 47

<400> SEQUENCE: 50

Met Trp Arg Val Pro Gly Thr Thr Arg Arg Pro Val Thr Gly Glu Ser
1               5                   10                  15
Pro Gly Met His Arg Pro Glu Ala Met Leu Leu Leu Thr Leu Ala
            20                  25                  30
Leu Leu Gly Gly Pro Thr Trp Ala Gly Lys Met Tyr Gly Pro Gly Gly
        35                  40                  45
```

PROTEIN SECRETORY FACTOR WITH HIGH SECRETORY EFFICIENCY AND AN EXPRESSION VECTOR COMPRISING THE SAME

The content of the electronically submitted sequence listing (Name: 2972_0060001_Sub_Seq_Listing.txt; size: 17,866 bytes; and Date of Creation: Sep. 14, 2017) is herein incorporated by reference in its entirety.

TECHNICAL FIELD

The present invention relates to a novel protein secretion factor, a vector including a nucleic acid sequence encoding the protein secretion factor, and a transformed cell into which the vector is introduced. Further, the present invention relates to a method of producing a target protein using a transformed cell including the vector.

BACKGROUND ART

A recombinant polypeptide or protein including an antibody is produced using various kinds of genetically-modified organisms including prokaryotic and eukaryotic cells. Many of the proteins used for medical treatment, research and the like are not suitable to be produced by prokaryotic cells such as bacteria because they are glycoproteins. For this reason, protein expression systems using eukaryotic cells such as yeast cells, insect cells or mammalian cells have been developed and widely used.

One of the major problems in the biotechnology for producing heterologous proteins is to produce and recover polypeptides, such as proteins and protein subunits), not easily expressed or secreted in genetically modified organisms. Since these proteins or protein subunits are expressed in cells at a very low level or a normal level, the scale of culturing and purifying tends to become larger in order to obtain a desired amount of proteins or protein subunits.

A typical method for solving such problems is to induce the proteins or protein subunits expressed in a cell to be secreted into a culture medium as high a level as possible. It is very useful even in purification to allow the proteins or protein subunits expressed in the cell to be secreted into an extracellular medium because these proteins are easily purified by doing so. In addition, the recombinant proteins or protein subunits secreted into an extracellular medium are advantageous in that protein decomposition occurring in the cell can be prevented and in that protein products with accurate folding can be obtained.

For successful secretion of the proteins expressed in a eukaryotic cell to the outside of the cell, a translocation of a protein traversing an intracellular endoplasmic reticulum is required. During the translocation, several modification steps required for protein activation occur concurrently, and thus the protein secreted to the outside of the cell can be considered as a mature protein which was immediately saccharified or modified.

Proteins secreted from a cell through a cell membrane are generally produced in the cell in the form of a precursor, and is referred to as a "preprotein". The preprotein includes an additional peptide sequence at the amino terminal ($NH_3$-terminal), and this peptide sequence allows the expressed protein to enter a secretion pathway by targeting this protein into an intracellular endoplasmic reticulum. This additional peptide sequence is referred to as a "protein secretion factor" or "signal sequence or signal peptide".

In the case of a recombinant protein, secretion may not operate as expected because the natural signal sequence of the recombinant protein does not operate well in a host cell. Although there are many known signal sequences that can be used for the secretion of a specific recombinant protein, there is still a need for the discovery of additional signal sequences capable of promoting the effective secretion of recombinant proteins, particularly, immunoglobulins in a mammalian host cell.

DISCLOSURE

Technical Problem

As such, the present inventors have made numerous efforts to develop a protein secretion factor capable of more effectively secreting and producing various recombinant proteins or target proteins. Accordingly, they developed a protein secretion factor capable of effectively secreting a target protein from an animal host cell to the outside thereof. In addition, they also found that an antibody could be effectively secreted and expressed using the developed protein secretion factor, thereby completing the present invention.

Technical Solution

An object of the present invention is to provide a novel protein secretion factor.

Another object of the present invention is to provide an expression cassette including a nucleic acid sequence encoding the protein secretion factor, which is linked to a gene encoding a target protein.

Still another object of the present invention is to provide a recombinant vector including a nucleic acid sequence encoding the protein secretion factor.

Still another object of the present invention is to provide a vector for secretory expression of target protein, which includes the expression cassette. Still another object of the present invention is to provide a transformed cell, into which the vector is introduced, into a host cell.

Still another object of the present invention is to provide a method of producing a target protein, including: culturing a transformed cell, into which a vector for expression of target protein secretion including the expression cassette is introduced to express a target protein and secrete the target protein to the outside of the cell; and recovering the target protein from a culture or a culture supernatant of the cell.

Still another object of the present invention is to provide use of the protein secretion factor for preparing a vector for secretory expression of target protein.

Still another object of the present invention is to provide use of the protein secretion factor for secreting target protein.

Advantageous Effects

When the protein secretion factor according to the present invention was used, the secretion of a target protein was remarkably increased, and, particularly, a remarkably excellent secretion effect for antibodies was exhibited, compared to when conventional protein secretion factors were used. Therefore, the protein secretion factor of the present invention can be widely used in the field of recombinant protein production, and particularly, in the field of antibody production.

BEST MODE

In one embodiment, the present invention provides a protein secretion factor.

In detail, the present invention provides a protein secretion factor having an amino acid sequence of SEQ ID NO: 1 or SEQ ID NO: 2.

As used herein, the term "protein secretion factor" means a factor linked to a protein to induce the protein to be secreted to the outside of a cell. Specifically, the protein secretion factor may be composed of a polypeptide. In the present invention, the protein secretion factor can be used together mixed with a signal sequence, a secretion sequence, a signal peptide (SP) or the like.

Specifically, the protein secretion factor may have an amino acid sequence selected from the group consisting of SEQ ID NOS: 1 to 8, and, more specifically, may have an amino acid sequence of SEQ ID NO: 1 or 2, but the present invention is not limited thereto.

The present inventors have identified a human gene LBFL313 with a pancreatic cancer marker differentially expressed in pancreatic adenocarcinoma tissues compared with normal pancreatic tissues through prior research (Korean Patent Application Publication No. 10-2007-0119250). The human gene LBFL313 identified in this way may have a cDNA sequence of SEQ ID NO: 47, but is not limited thereto. It is known that this human gene can be used as a diagnostic agent or marker for detecting pancreatic cancer or identifying normal tissues and pancreatic adenocarcinoma in a sample, but whether or not this gene has a secretion factor has not been known.

In an exemplary embodiment of the present invention, the present inventors have selected peptide sequences presumably having a potential to be used as a secretion factor while analyzing the configuration of the newly-identified gene. As a result, they determined secretion factor candidates (SP7.2 and SP7.3) having an amino acid sequence of SEQ ID NO: 1 and SEQ ID NO: 2. After determining the secretion factor candidates, their secretagogue capabilities were compared with those of six known secretion factors (SP1 to SP6).

Figure 9:
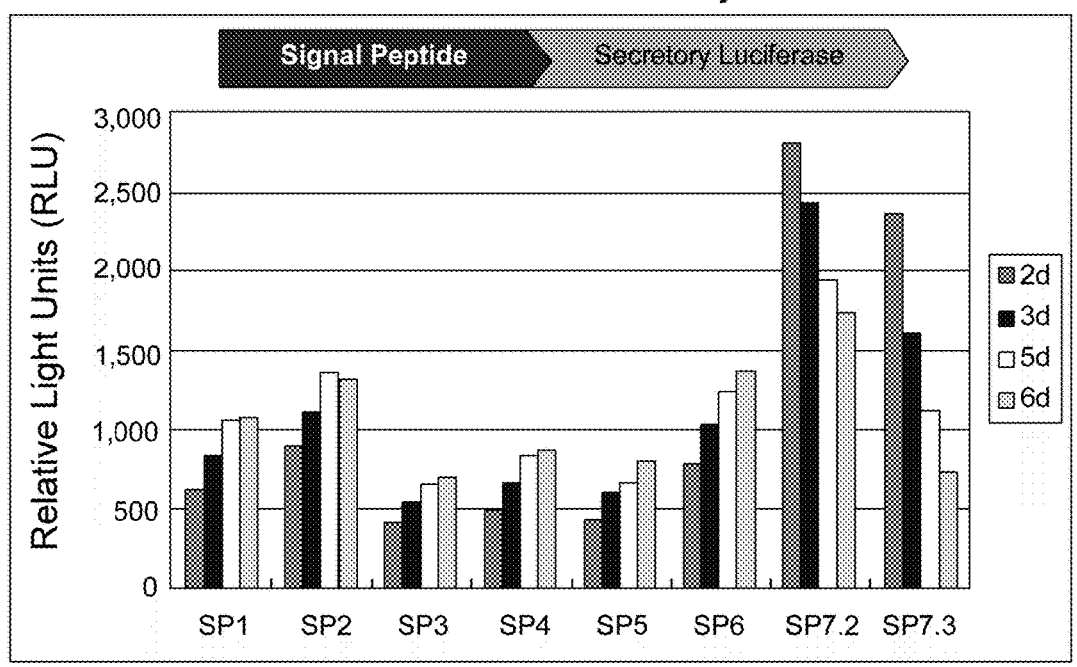
FIG. 9 is a graph showing the results of the secretion amount of a luciferase present in a culture medium, measured on the 2nd, 3rd, 5th, and 6th day after eight different types of plasmid vectors (pCBIN-CLUCL pCBIN-CLUC2, pCBIN-CLUC3, pCBIN-CLUC4, pCBIN-CLUC5, pCBIN-CLUC, pCBIN-CLUC7.2 and pCBIN-CLUC7.3) were transformed into a CHO cell line, into each of which a luciferase gene prepared by the present inventors was inserted.

As the result of measuring the luciferase secretion efficacy of each of the secretion factors, two signal sequences having an amino acid sequence of SEQ ID NO: 1 or SEQ ID NO: 2 and derived from gene LBFL313 were shown to improve the level of luciferase secretion compared to the conventional signal sequence (SP1) (refer to FIG. 9). Particularly, in the case of SP7.2 and SP7.3 vectors, a very large amount of luciferase was secreted at the early stage of culture (2d and 3d).

The protein secretion factor can be used to promote the secretion of a target protein.

As used herein, the target protein refers to a protein intended to be expressed and secreted in a desired host cell using the protein secretion factor. A nucleic acid sequence encoding the target protein can be named "gene of interest".

In the present invention, the target protein may be a protein intrinsically expressed in a host cell or a protein expressed by a foreign gene introduced thereinto. The kind of the target protein is not particularly limited as long as extracellular secretion efficiency is increased by the protein secretion factor.

Examples of the target protein may include an antibody, a human growth hormone, a serum protein, immunoglobulin, cytokine, α-, β- or γ-interferon, a colony-stimulating factor (GM-CSF), a platelet-derived growth factor (PDGF), a phospholipase-activating protein (PLAP), insulin, a tumor necrosis factor (TNF), a growth factor, a hormone, calcitonin, a calcitonin gene related peptide (CGRP), enkephalin, somatomedin, erythropoietin, a hypothalamic secretion factor, prolactin, chronic gonadotropin, a tissue plasminogen activator, a growth hormone releasing peptide (GHRP), a thymic humoral factor (THF), asparaginase, arginase, arginine deaminase, adenosine deaminase, aminase, peroxide dismutase, endotoxinase, catalase, chymotrypsin, lipase, uricase, adenosine diphosphatase, tyrosinase, bilirubin oxidase, glucose oxidase, glucosidase, galactosidase, glucocerebrosidase, and glucourodinase. Specific examples thereof may include heavy-chain and light-chain proteins, but are not limited thereto. Here, the antibody is a concept including full-length antibodies, Fc fragments, and antibody fragments such as Fab, Fab', F(ab')$_2$, and Fv. In addition, the antibody light chain may have an amino acid sequence of SEQ ID NO: 48, and the antibody heavy chain may have an amino acid sequence of SEQ ID NO: 49, but are not limited thereto.

The protein secretion factor can be linked to a target protein. Specifically, the protein secretion factor is designed to be linked to a target protein in frame, thereby causing the secretory expression of a target protein in a host cell.

Meanwhile, a nucleic acid sequence encoding the protein secretion factor linked to a gene encoding a target protein is a concept that includes the direct linkage of the nucleic acid sequence and the gene and/or the linkage thereof through a linker.

The example of linker may include an affinity tag and/or a protease recognition sequence.

Examples of the affinity tag may include GST, MBP, NusA, thioredoxin, ubiquitin, FLAG, BAP, 6HIS, STREP, CBP, CBD, and S-tag, but are not limited to, and various affinity tags known in the art may be used.

Examples of the protease recognition sequence may include sequences recognized by mammal purine, factor Xa, enterokinase, subtilisin, tobacco etch virus protease, and ubiquitin hydrolase, but are not limited to, and various protease recognition sequences known in the art may be used.

In another embodiment, the present invention provides an expression cassette including a nucleic acid sequence encoding the protein secretion factor which is linked to a gene encoding a target protein.

In the present invention, the protein secretion factor, target protein, and the like are the same as those described above.

As used herein, the term "expression cassette" refers to a sequence regulating one or more genes and expression thereof, that is, a nucleic acid sequence including any combination of various cis-acting transcription regulating elements. The expression cassette of the present invention may further include various elements, for example, nucleic acid sequences such as a promoter and an enhancer, which are recognized in the art to be necessary for expression regulation, as well as the nucleic acid sequence encoding a protein secretion factor and a target protein. The sequence regulating the expression of a gene, that is, the sequence regulating the transcription of a gene and the expression of the transcription product thereof, is generally referred to as a "regulatory unit". Most of the regulatory unit is located upstream of a coding sequence of a target gene such that it is operably linked thereto. In addition, the expression cassette may include a 3' non-transcriptional region including a poly-adenylation site at a 3' terminal.

The expression cassette includes a promoter sequence and a nucleic acid sequence encoding a fusion protein in which the protein secretion factor and the target protein are linked, and is configured such that the promoter sequence is functionally linked to the nucleic acid sequence encoding the fusion protein.

Here, the term "functionally linked" means that one DNA region is functionally linked to another DNA region. For example, a desired gene sequence is functionally linked to an expression regulating sequence such as a promoter to allow the desired gene to be expressed by the activation of the promoter.

In the present invention, the expression cassette includes a promoter sequence, and a nucleic acid sequence encoding a protein secretion factor having an amino acid sequence of SEQ ID NO: 1 or SEQ ID NO: 2, which is linked to a gene encoding a target protein, and is designed to realize the extracellular secretory expression of a target protein in a host cell, and particularly, in an animal host cell.

In still another embodiment, the present invention provides a recombinant vector including a nucleic sequence encoding the protein secretion factor.

More specifically, the present invention provides a vector for expression of target protein secretion, including a nucleic acid sequence encoding a protein secretion factor which is linked to a gene encoding the target protein.

The protein secretion factor, the target protein, and the linkage of the protein section factor and the target protein are the same as described above.

Further, the vector for expression of target protein secretion according to the present invention may further include an expression cassette including a nucleic acid sequence encoding a protein secretion factor, which is linked to a gene encoding a target protein, selected from the group consisting of SEQ ID NOS: 1 to 8.

Moreover, the vector for expression of target protein secretion according to the present invention may be a vector for secretory expression of antibody.

For example, the vector for expression of target protein secretion may include: a) a first expression cassette including a nucleic acid sequence encoding a protein secretion factor, which is linked to a gene encoding an antibody light chain; and b) a second expression cassette including a nucleic acid sequence encoding a protein secretion factor, which is linked to a gene encoding an antibody heavy chain.

Specifically, the vector for secretory expression of an antibody may include: a) a first expression cassette including a nucleic acid sequence encoding a protein secretion factor having an amino acid sequence of SEQ ID NO: 1 or SEQ ID NO: 2, which is linked to a gene encoding an antibody light chain; and b) a second expression cassette including a nucleic acid sequence encoding a protein secretion factor having an amino acid sequence selected from the group consisting of SEQ ID NOS: 1 to 8, which is linked to an antibody heavy chain. For example, the protein secretion factor of b) may be a protein secretion factor having an amino acid sequence of SEQ ID NO: 3.

More specifically, the protein secretion factor of a) may be a protein secretion factor having an amino acid sequence of SEQ ID NO: 1, and the protein secretion factor of b) may be a protein secretion factor having an amino acid sequence of SEQ ID NO: 3. Here, the antibody light chain may be composed of an amino acid sequence of SEQ ID NO: 48, and the antibody heavy chain may be composed of an amino acid sequence of SEQ ID NO: 49, but the present invention is not limited thereto.

As used herein, the term "vector for secretory expression of target protein" refers to an expression vector, which includes a nucleic acid encoding a protein secretion factor, which is linked to a gene encoding a target protein to cause the extracellular secretion of a target protein at the time of introducing the vector into a host cell and expressing this vector.

As used herein, the term "expression vector" refers to a double-stranded DNA fragment as a carrier into which a target DNA fragment is inserted. The expression vector used in expressing a protein in the art may be used without limitation. Here, the target DNA refers to a DNA encoding a target protein intended to be expressed. Once the expression vector is in a host cell, this expression vector can be replicated regardless of a host chromosomal DNA, and the inserted target DNA can be expressed. As well known in the art, in order to increase the expression level of a transfected gene in a host cell, the transfected gene must be operably linked to a transcription and decoding expression regulating sequence allowing the gene to exhibit a function in the selected host cell.

In an exemplary embodiment of the present invention, based on the pTOP-BA-RL-pA vector having 'CMVe', 'CB' and 'Beta-actin Intron' (Korean Patent Application Publication No. 10-2012-0059222), a vector for expression of target protein secretion was prepared by operably liking a nucleic acid sequence encoding a protein secretion factor composed of amino acid sequences of SEQ ID NOS: 1 to 8 with a gene encoding a protein to be produced.

In the specific embodiment of the present invention, the present inventors prepared an antibody expression vector (Example 5) by selecting SP2 (SEQ ID NO: 4), SP6 (SEQ ID NO: 8) and SP7.2 (SEQ ID NO: 1) from among the signal sequences exhibiting excellent secretion inducing effects in the luciferase secretion measurement test in order to confirm whether the prepared antibody expression vector exhibit excellent secretion inducing ability even to a monoclonal antibody, for which an industrial large-scale production is required. In this test, an Rx antibody was used as the monoclonal antibody, and the Rx antibody includes an antibody light chain composed of an amino acid sequence of SEQ ID NO: 48 and an antibody heavy chain composed of an amino acid sequence of SEQ ID NO: 49.

In order to determine the optimal configuration of an antibody secretion factor, the secretion factors of the antibody light chain and antibody heavy chain were differently combined, and the secretion efficiency thereof was examined.

That is, the antibody light chain and antibody heavy chain were expressed from the vector prepared by linking the signal sequences selected from the group consisting of SP1 (SEQ ID NO: 3), SP2 (SEQ ID NO: 4), SP6 (SEQ ID NO: 8), and SP7.2 (SEQ ID NO: 1) to the antibody light chain and antibody heavy chain, respectively, and the secretion efficiency thereof was examined.

In order to examine the extracellular secretion efficiency of the signal sequence in in-vitro cell culture system, the signal sequence was transformed into a CHO cell, and then the secretion level of a monoclonal antibody was examined via ELISA.

Figure 12:
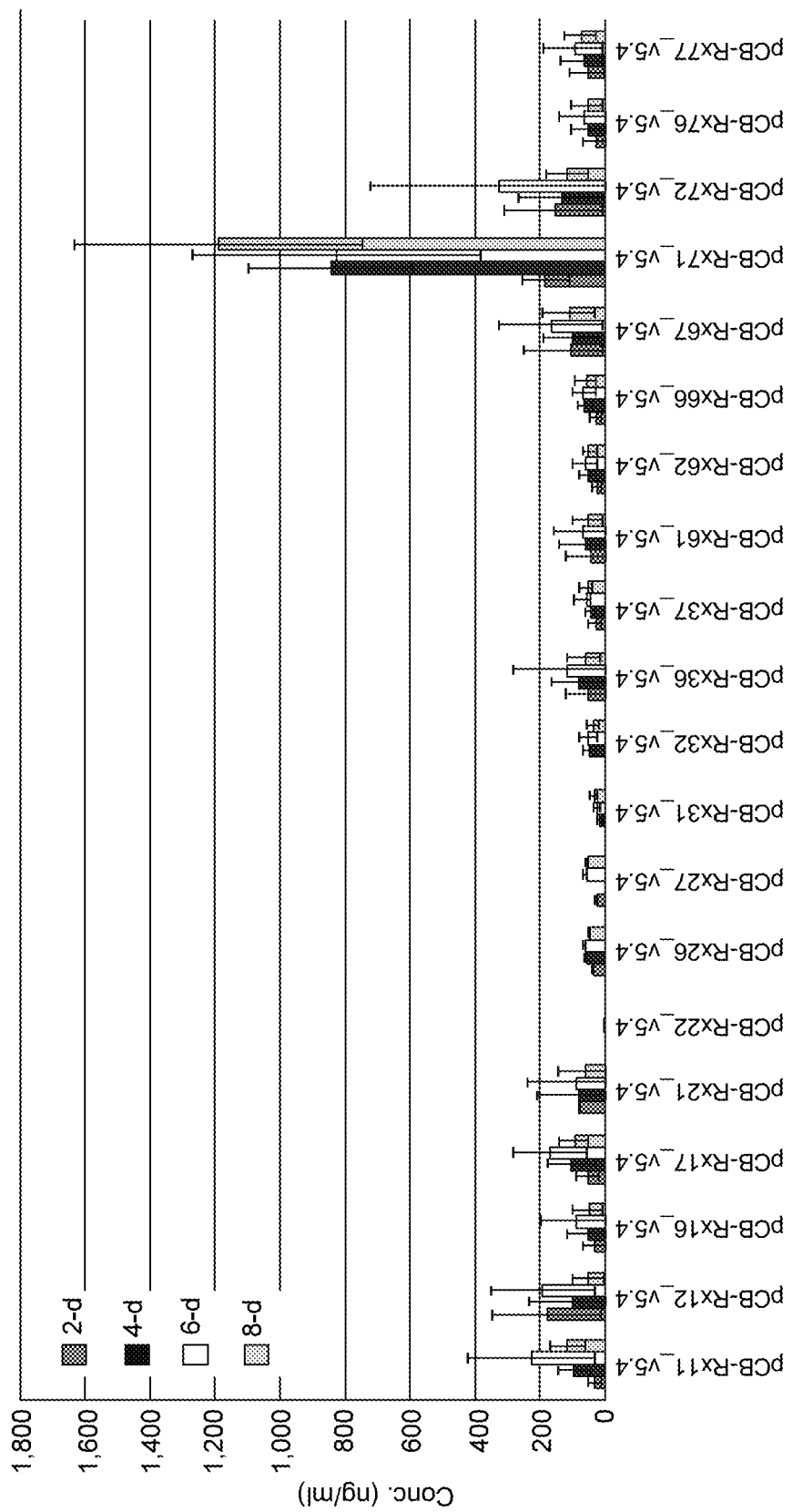
FIG. 12 is a graph showing the antibody secretion ability depending on the combination of protein secretion factors linked to light-chain and heavy-chain genes of an Rx antibody, which was measured by enzyme-linked immunosorbent assay (ELISA).

As a result of measuring the secretion level of an antibody via ELISA assay, high secretion level was confirmed from expression vector pCB-Rx71_v5.4 including the SP7.2 signal sequence encoding an amino acid sequence of SEQ ID NO: 1 derived from the LBFL313 gene (refer to FIG. 12). Particularly, a significantly high level of secretion was observed from the combination of the SP7.2 signal sequence linked to an antibody light chain and the SP1 signal sequence encoding an amino acid sequence of SEQ ID NO: 3 and linked to the antibody heavy chain. Further, it was confirmed that the secretion level increased further along with the increase in culture period. Consequently, it was confirmed that, when the SP7.2 signal sequence was used, the secretion level was remarkably increased even in a long-term culture, compared to the results of the luciferase secretion test, in which the secretion level was remarkably increased in a short-term culture.

In still another embodiment, the present invention provides a transformed cell in which the vector is introduced into a host cell.

As used herein, the term "transformation" means that DNA is introduced into a host cell, and thus the DNA is made replicable by chromosomal integration. In the present invention, the host cell that can be used in the transformation in the present invention may include a prokaryotic or/and a eukaryotic cell.

In the present invention, examples of the host cell may include bacteria; generally known prokaryotic and eukaryotic hosts such as *Escherichia, Pseudomonas, Bacillus, Streptomyces*, fungi, and yeasts; insect cells such as *Spodoptera frupperda* (SF9); and animal cells such as CHO, COS 1, COS 7, BSC 1, BSC 40, and BMT 10. In the present invention, the host cell may be an animal host cell, and particularly a Chinese Hamster Ovary Cell (CHO) cell, but is not limited thereto.

In an exemplary embodiment of the present invention, a Chinese Hamster Ovary (CHO) cell, which is widely used in the production of a recombinant protein, was as the host cell.

In still another embodiment, the present invention provides a method of producing a target protein, including: i) culturing a transformed cell, into which the vector for secretory expression of target protein is introduced, to express a target protein and secrete the target protein to the outside of the cell; and ii) recovering the target protein from a culture or a culture supernatant of the cell.

The method of producing a target protein may further include purifying the recovered target protein. If necessary, the purification of the target protein may be performed by a protein purification method generally used in the art. For example, the target protein can be separated from the culture or culture supernatant of the host cell by a conventional chromatography method, such as immunoaffinity chromatography, receptor affinity chromatography, hydrophobic interaction chromatography, lectin affinity chromatography, size exclusion chromatography, cation or anion exchange chromatography, high performance liquid chromatography (HPLC) or reversed-phase high-performance liquid chromatography. Meanwhile, when the target protein is a fusion protein having an idiosyncratic tag, label or chelate moiety, this target protein may be purified using an idiosyncratic binding partner or agent. The purified protein may be cleaved into desired protein parts by removing a protein secretion factor or may remain in itself. In the process of cleaving a fusion protein, a desired protein having additional amino acid can be made.

In the present invention, the protein secretion factor, protein, expression cassette, target protein, vector for secretory expression, transformation, host cell, and the like are the same as described above.

The host cell used in the method may be an animal host cell, and particularly, a Chinese Hamster Ovary (CHO) cell. Further, the transformed host cell, if necessary, may be cultured by a general culture method known in the art.

In still another embodiment, the present invention provides use of the protein secretion factor for preparing a vector for secretory expression of target protein.

The protein secretion factor, the vector and target protein are the same as described above.

In still another embodiment, the present invention provides use of the protein secretion factor for secreting target protein.

The protein secretion factor, the vector and target protein are the same as described above.

MODE FOR INVENTION

Hereinafter, the present invention will be described in more detail with reference to Examples below. However, these Examples are set forth only to illustrate the present invention, and the scope of the present invention is not limited to these Examples.

Example 1: Molecular Biology Technique

Methods generally used in molecular biology, such as restriction enzyme treatment, agarose gel electrophoresis, Gel Extraction Kit (QIAGEN), plasmid DNA purification, polymerase chain reaction (PCR), ligation of DNA fragments, and transformation of E. coli, were performed according to the methods described in the literature (Sambrook J et al., 2001 Molecular cloning: A laboratory manual, 2nd edition. Cold Spring Harbor Laboratory Press, Cold Spring Harbor, N.Y.) with minimum modifications.

Example 2: Selection of Signal Sequences 2-1: Test Method

In order to identify a signal sequence for enhancing secretion during the process of expressing a heterologous protein using an animal host cell, the possibility for a high-efficiency secretory signal sequence was intended to be examined from the literature "novel gene LBFL313 related to pancreatic cancer" disclosed in Korean Patent No. 10-0954322.

Specifically, peptide sequences, presumed to have a potential as signal sequences, were selected from an LBFL313 gene, and these selected peptide sequences were compared with the conventional six signal sequences generally used as signal sequences in animal cells. In this regard, as a first comparison test, a Chinese hamster ovary (CHO) cell line widely used in the production of a recombinant protein was used as a host cell, and a secretory luciferase gene was used as a target gene. The secretion level was determined by measuring the amount of the light emitted by the oxidation of luciferin (used as a substrate) by a luciferase secreted to the outside of a cell using a luminometer.

Thereafter, as a second comparison test for comparing the secretion of a monoclonal antibody, which is an industrially available protein, instead of a luciferase, to that of the signal sequences selected in the first comparison test, the amount of the antibodies secreted by various combinations of the signal sequence of the light chain and the signal sequence of the heavy chain of the antibodies was measured via ELISA using a CHO cell line as a host cell. Here, the antibody secreted to the outside of cell was fixed by covering an ELISA plate with F(ab')$_2$ recognizing the Fc portion of the heavy chain, and the antibody bonded to the kappa portion of the light chain was marked with a horseradish peroxidase (HRP), and the oxidation of TMB used as a substrate was measured using a spectrophotometer, thereby determining the secretion level.

2-2: Signal Sequence Used in Test

The peptide sequences expected as signal sequences were presumed from the LBFL313 gene in Example 2-1. As a result, SP7.2 and SP7.3 were selected.

X SP7.2
(SEQ ID NO: 1)
NH$_3$-MHRPEAMLLLLTLALLGGPTWA-CO$_2$H

X SP7.3
(SEQ ID NO: 2)
NH$_3$-MWRVPGTTRRPVTGESPGMHRPEAMLLLLTLALLGGPTWA-CO$_2$H

The six conventional signal sequences used for comparison test with the above-selected signal sequences were named SP1 to SP6. These signal sequences are as follows.

X SP1
(SEQ ID NO: 3)
NH$_3$-MGWSYIILFLVATATDVHS-CO$_2$H

X SP2
(SEQ ID NO: 4)
NH$_3$-MKWVTFISLLFLFSSAYSRGVFRR-CO$_2$H

X SP3
(SEQ ID NO: 5)
NH$_3$-MDFQVQIISFLLISASVIMSRG-CO$_2$H

X SP4
(SEQ ID NO: 6)
NH$_3$-MGWSLILLFLVAVATRVLS-CO$_2$H

X SP5
(SEQ ID NO: 7)
NH$_3$-MLLLLLLLGLRLQLSLG-CO$_2$H

X SP6
(SEQ ID NO: 8)
NH$_3$-MKTLILAVALVYCATVHC-CO$_2$H

In this test, SP1 is a signal sequence derived from mouse IgG2; SP2 is a signal sequence derived from human serum albumin (HSA); SP3 is a signal sequence derived from mouse IkC; SP4 is an artificially synthesized signal sequence (not a natural signal sequence) and is a signal sequence used in U.S. Pat. No. 7,381,560; SP5 is a signal sequence derived from a secretory alkaline phosphatase (SEAP); and SP6 is a signal sequence derived from Cypridina noctiluca luciferase (CLUC), which is a secretory luciferase.

In this test, in order to select plasmid vectors exhibiting high target protein secretion from among such plasmid vectors by optimal combination, typically, a Cypridina noctiluca luciferase (CLUC) gene, which is an easily-measurable secretory luciferase, and an Rx antibody gene, which is an IgG1 type antibody gene, were used as a reporter.

The following various combinations of plasmid vectors were prepared by linking DNA sequences encoding the eight signal sequences with gene sequences (Cypridina noctiluca luciferase (CLUC) gene or light chain and heavy chain genes of an Rx antibody, which is an IgG1 type antibody) in frame. The combinations and components of the thus prepared plasmid vectors are summarized in Table 1 below.

TABLE 1

| Plasmid name | Components |
|---|---|
| pCBIN-CLUC1 | SP1 + CLUC |
| pCBIN-CLUC2 | SP2 + CLUC |
| pCBIN-CLUC3 | SP3 + CLUC |
| pCBIN-CLUC4 | SP4 + CLUC |
| pCBIN-CLUC5 | SP5 + CLUC |
| pCBIN-CLUC | SP6 + CLUC |
| pCBIN-CLUC7.2 | SP7.2 + CLUC |
| pCBIN-CLUC7.3 | SP7.3 + CLUC |
| pCB-Rx11_v5.4 | (SP1 + antibody light chain) + (SP1 + antibody heavy chain) |
| pCB-Rx12_v5.4 | (SP1 + antibody light chain) + (SP2 + antibody heavy chain) |
| pCB-Rx16_v5.4 | (SP1 + antibody light chain) + (SP6 + antibody heavy chain) |
| pCB-Rx17_v5.4 | (SP1 + antibody light chain) + (SP7.2 + antibody heavy chain) |
| pCB-Rx21_v5.4 | (SP2 + antibody light chain) + (SP1 + antibody heavy chain) |

TABLE 1-continued

| Plasmid name | Components |
|---|---|
| pCB-Rx22_v5.4 | (SP2 + antibody light chain) + (SP2 + antibody heavy chain) |
| pCB-Rx26_v5.4 | (SP2 + antibody light chain) + (SP6 + antibody heavy chain) |
| pCB-Rx27_v5.4 | (SP2 + antibody light chain) + (SP7.2 + antibody heavy chain) |
| pCB-Rx31_v5.4 | (SP3 + antibody light chain) + (SP1 + antibody heavy chain) |
| pCB-Rx32_v5.4 | (SP3 + antibody light chain) + (SP2 + antibody heavy chain) |
| pCB-Rx36_v5.4 | (SP3 + antibody light chain) + (SP6 + antibody heavy chain) |
| pCB-Rx37_v5.4 | (SP3 + antibody light chain) + (SP7.2 + antibody heavy chain) |
| pCB-Rx61_v5.4 | (SP6 + antibody light chain) + (SP1 + antibody heavy chain) |
| pCB-Rx62_v5.4 | (SP6 + antibody light chain) + (SP2 + antibody heavy chain) |
| pCB-Rx66_v5.4 | (SP6 + antibody light chain) + (SP6 + antibody heavy chain) |
| pCB-Rx67_v5.4 | (SP6 + antibody light chain) + (SP7.2 + antibody heavy chain) |
| pCB-Rx71_v5.4 | (SP7.2 + antibody light chain) + (SP1 + antibody heavy chain) |
| pCB-Rx72_v5.4 | (SP7.2 + antibody light chain) + (SP2 + antibody heavy chain) |
| pCB-Rx76_v5.4 | (SP7.2 + antibody light chain) + (SP6 + antibody heavy chain) |
| pCB-Rx77_v5.4 | (SP7.2 + antibody light chain) + (SP7.2 + antibody heavy chain) |

In the test using CLUC, the extracellular secretion level was measured via luciferase assay, and in the test using the Rx antibody, the extracellular secretion level was measured via ELISA assay.

Example 3: Preparation of Luciferase Plasmid Vectors

Plasmid vectors having the secretory sequences designed in Example 2-2 and having a secretory luciferase (CLUC) as a reporter gene were prepared.

3-1: Preparation of pCBIN-CLUC6

Figure 1:
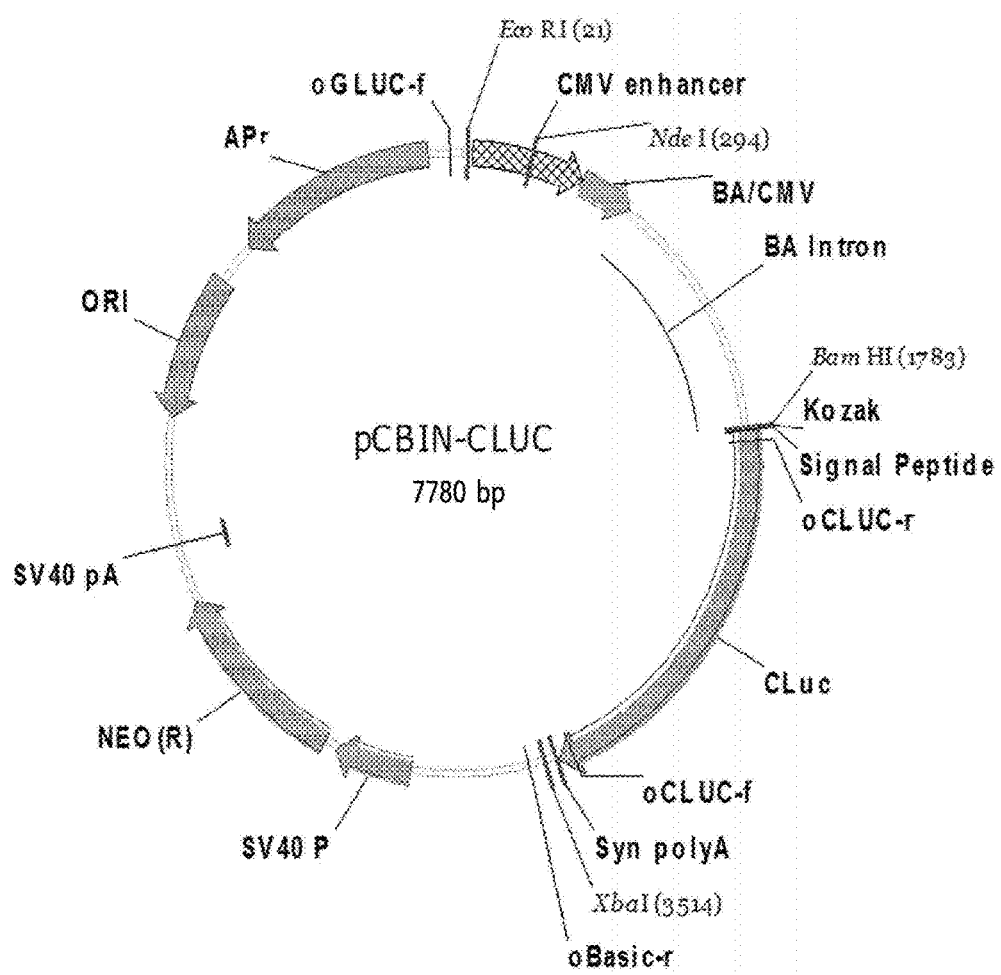
FIG. 1 shows a plasmid map of a luciferase expression vector pCBIN-CLUC having a protein secretion factor SP6 prepared by the present inventors.

In order to construct a reporter vector having a CMV enhancer (CMVe) and a CMV/beta-actin fusion promoter (CB), a DNA fragment (1762 bp), which was obtained by treating a pTOP-BA-RL-pA vector having 'CMVe', 'CB' and 'beta-actin intron' (disclosed in Korean Patent Application Publication No. 10-2012-0059222) with EcoRI and BamHI, was inserted into a pCLuc-Basic2 vector (NEB, Cat#: N0317S) digested by the same restriction enzyme. The reporter vector constructed in this way has a signal sequence 'SP6' (pCBIN-CLUC) (refer to FIG. 1).

3-2: Preparation of pCBIN-CLUC1

Figure 2:
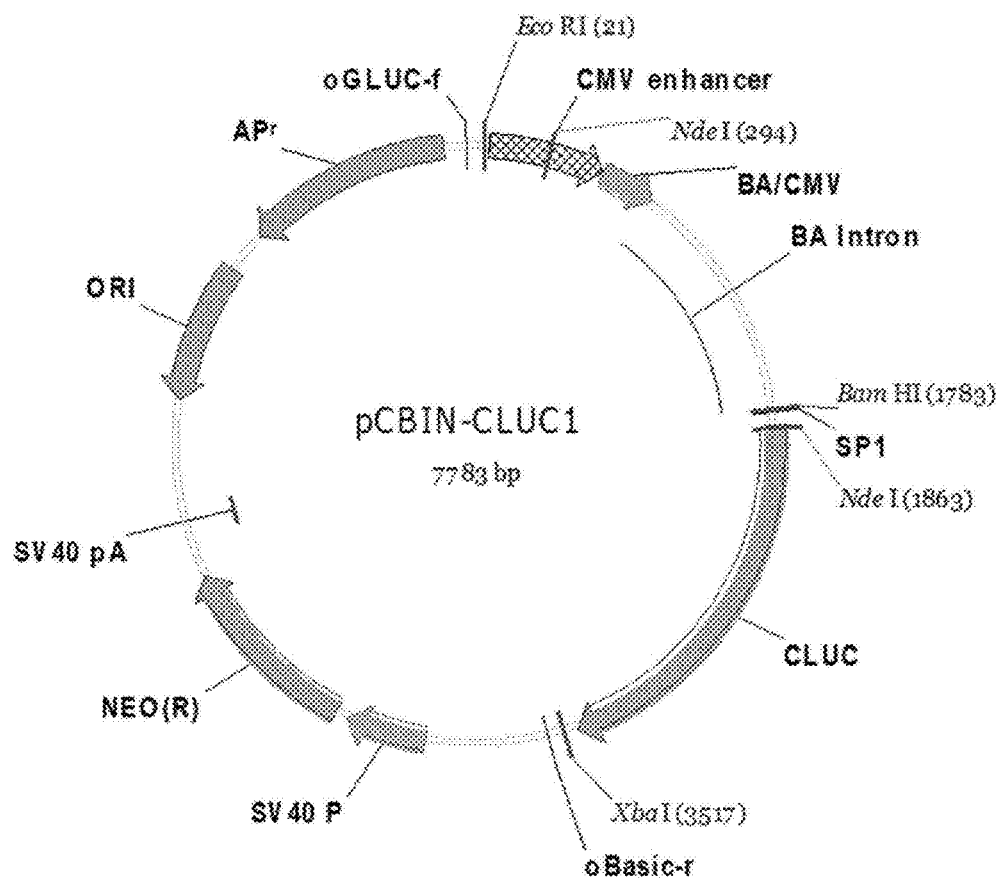
FIG. 2 shows a plasmid map of a luciferase expression vector pCBIN-CLUC1 having a protein secretion factor SP1 prepared by the present inventors.

A DNA fragment (80 bp), which was obtained via PCR amplification of a DNA sequence encoding a peptide sequence of a mouse IgG2 signal sequence (SP1: SEQ ID NO: 3) using two primers of SEQ ID NOS: 9 and 10 using pCB-Ix6_v5.4 as a template and then digesting the PCR-amplified product with BamHI and NdeI, and a DNA fragment (1654 bp), which was obtained via PCR amplification a CLUC gene using two primers (SEQ ID NOS: 11 and 12) and the pCLuc-Basic2 vector as a template and then digesting the PCR-amplified product with NdeI and XbaI, were inserted into the site of a DNA fragment (6049 bp), which was obtained by digesting the pCBIN-CLUC vector with BamHI and XbaI, so as to prepare a pCBIN-CLUC1 vector (refer to FIG. 2).

The primers used are as follows.

※ oSP1-f
(SEQ ID NO: 9)
5'-tt GGATCC gcc acc atg gga tgg agc tat-3'

※ oSP1-r
(SEQ ID NO: 10)
5'-ttC ATA TGg aca gtc ctg gga gtg gac atc tgt-3'

※ oCLUC-N1-f
(SEQ ID NO: 11)
5'-tt c CATATG aa cct gat cca cca aa-3'

※ oBasic-r
(SEQ ID NO: 12)
5'-tca gaa gcc ata gag ccc acc gca t-3'

3-3: Preparation of pCBIN-CLUC2

Figure 3:
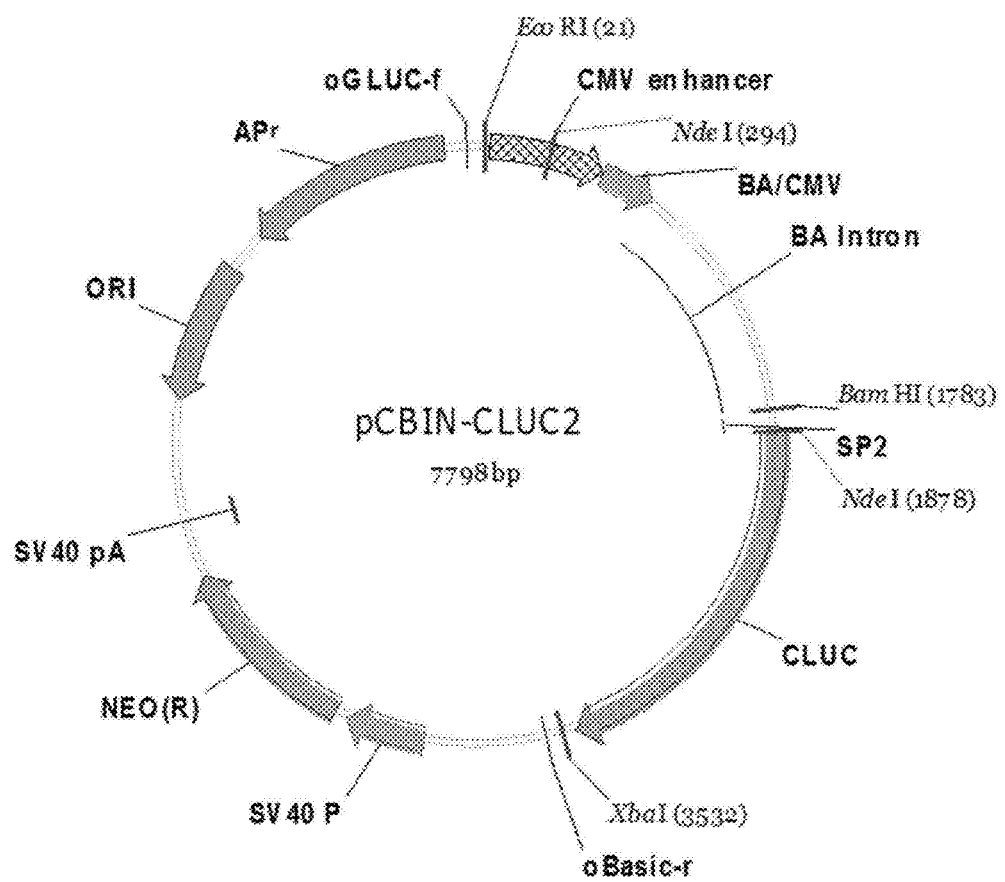
FIG. 3 shows a plasmid map of a luciferase expression vector pCBIN-CLUC2 having a protein secretion factor SP2 prepared by the present inventors.

A DNA fragment (95 bp), which was obtained by annealing a DNA sequence encoding a peptide sequence of a human serum albumin (HAS) signal sequence to two oligonucleotides (SEQ ID NOS: 13 and 14) to use the annealed DNA sequence as a template, amplifying the resulting DNA sequence via PCR using two primers (SEQ ID NOS: 15 and 16) and then digesting the PCR-amplified product with BamHI and NdeI, and a DNA fragment (1654 bp), which was obtained via PCR amplification a CLUC gene using two primers (SEQ ID NOS: 11 and 12) using the pCLuc-Basic2 vector as a template and then cleaving the PCR-amplified product using NdeI and XbaI were inserted into the cleft site of a DNA fragment (6049 bp), which was obtained by digesting the pCBIN-CLUC vector with BamHI and XbaI, so as to prepare a pCBIN-CLUC2 vector (refer to FIG. 3).

The primers used are as follows.

※ oHSAL-U
(SEQ ID NO: 13)
5'-atg aag tgg gtg acc ttc atc tcc ctg ctg ttc ctg ttc tcc tcc gcc tac tcc agg ggc gtg ttc agg agg-3'

※ oHSAL-L
(SEQ ID NO: 14)
5'-cct cct gaa cac gcc cct gga gta ggc gga gga gaa cag gaa cag cag gg-3'

※ oSP2-f
(SEQ ID NO: 15)
5'-tt GGATCC gcc acc atg aag tgg gtg acc-3'

※ oSP2-r
(SEQ ID NO: 16)
5'-ttC ATA TGg aca gtc ctg cct cct gaa cac gcc -3'

3-4: Preparation of pCBIN-CLUC3

Figure 4:
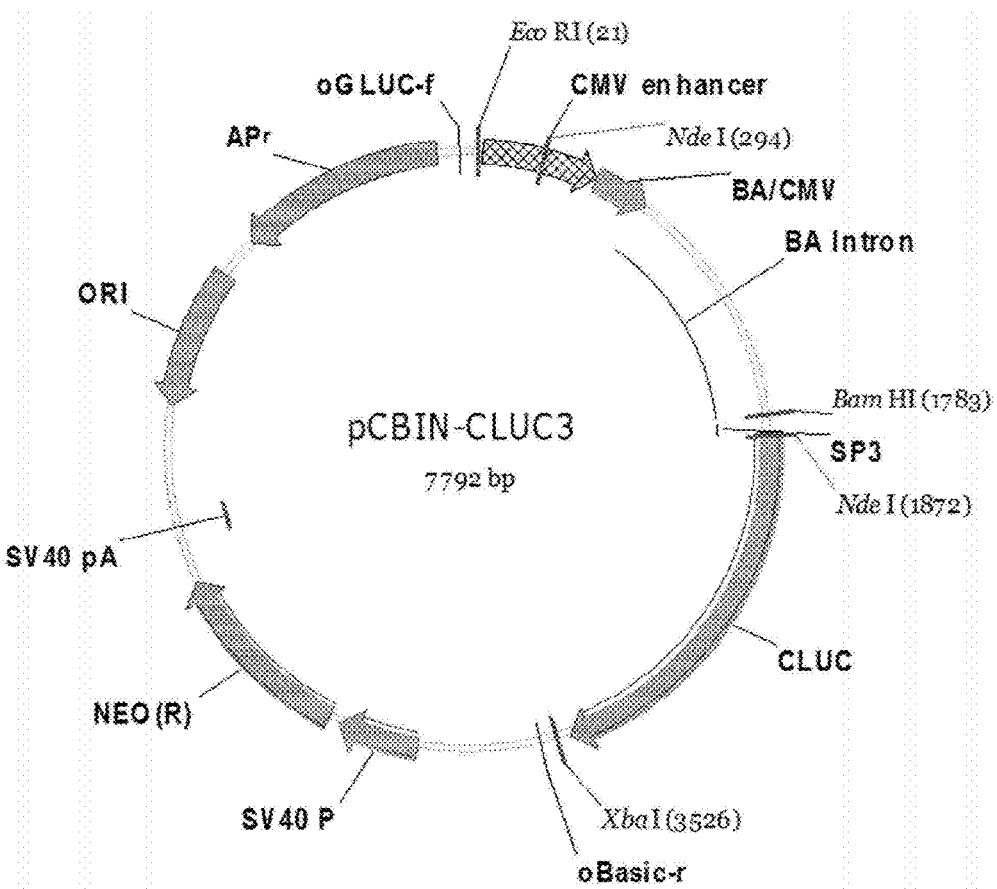
FIG. 4 shows a plasmid map of a luciferase expression vector pCBIN-CLUC3 having a protein secretion factor SP3 prepared by the present inventors.

A DNA fragment (89 bp), which was obtained via PCR amplification using two primers of SEQ ID NOS: 17 and 18 using a pCB-Rx vector (expression vector retained by our company, in which 'SP3' and 'SP4' were used as signal sequences) expressing a mouse-human chimeric IgG1 monoclonal antibody as a template and then digesting the PCR-amplified product with BamHI and NdeI, and a DNA fragment (1654 bp), which was obtained via PCR amplification of via PCR amplification a CLUC gene using two primers (SEQ ID NOS: 11 and 12) and the pCLuc-Basic2 vector as a template, and then digesting the PCR-amplified product with NdeI and XbaI were inserted into the restriction site of a DNA fragment (6049 bp), which was obtained by digesting the pCBIN-CLUC vector with BamHI and XbaI, so as to prepare a pCBIN-CLUC3 vector (refer to FIG. 4).

The primers used are as follows.

❋ oSP3-f
(SEQ ID NO: 17)
5'-tt GGATCC gcc acc atg gac ttc cag gtg-3'

❋ oSP3-r
(SEQ ID NO: 18)
5'-ttC ATA TGg aca gtc ctg gcc cct gga cat gat -3'

3-5: Preparation of pCBIN-CLUC4

Figure 5:
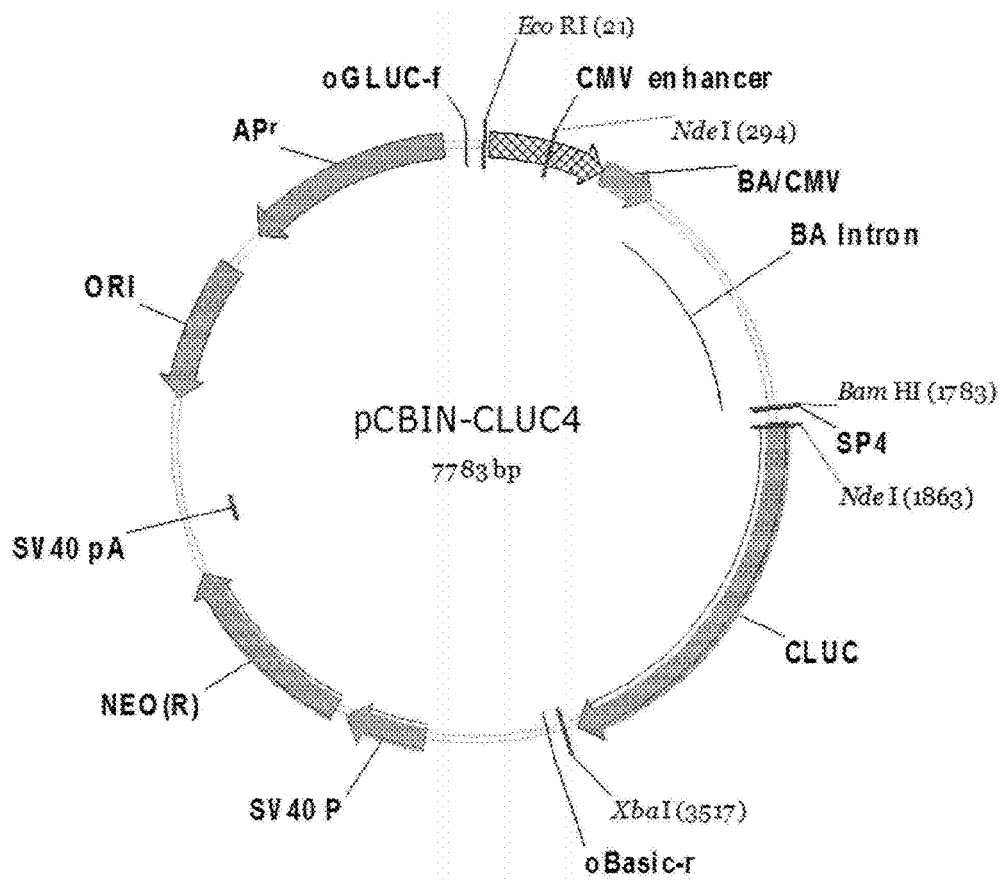
FIG. 5 shows a plasmid map of a luciferase expression vector pCBIN-CLUC4 having a protein secretion factor SP4 prepared by the present inventors.
Figure 6:
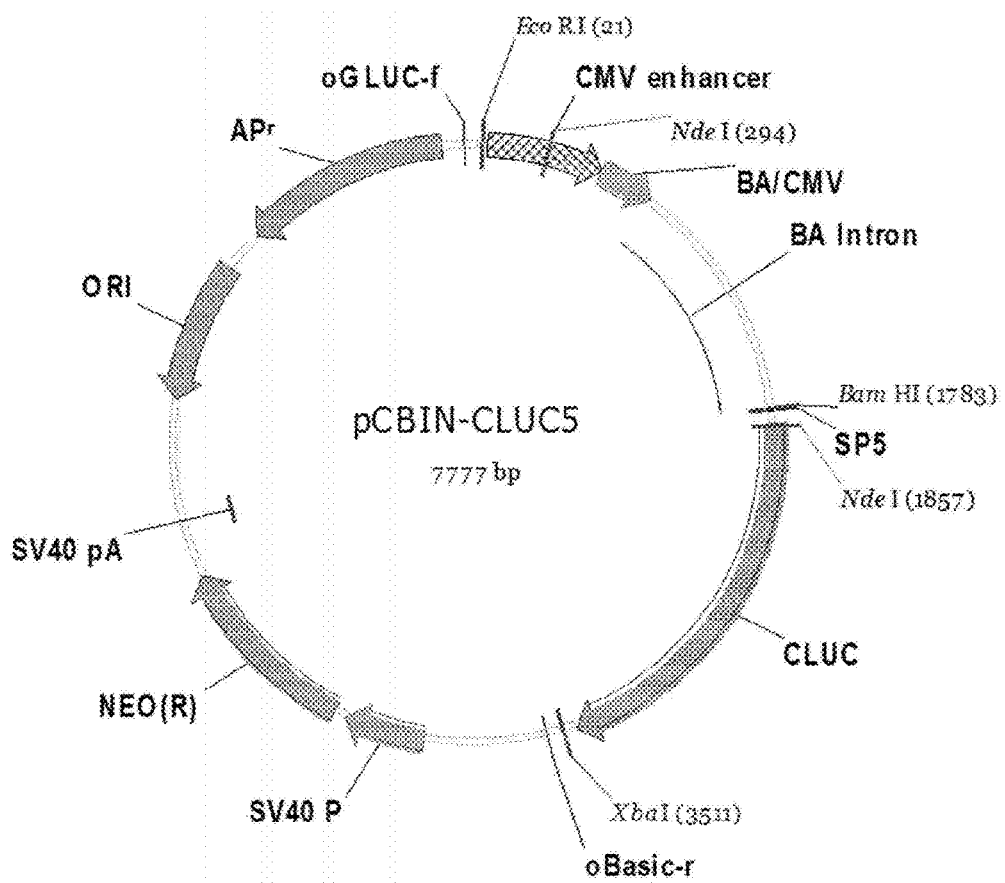
FIG. 6 shows a plasmid map of a luciferase expression vector pCBIN-CLUC5 having a protein secretion factor SP5 prepared by the present inventors.

A DNA fragment (80 bp), which was obtained via PCR amplification using two primers of SEQ ID NOS: 19 and 20 and a pCB-Rx vector expressing a mouse-human chimeric IgG1 monoclonal antibody as a template and then digesting the PCR-amplified product with BamHI and NdeI, and a DNA fragment (1654 bp), which was obtained via PCR amplification a CLUC gene using two primers (SEQ ID NOS: 11 and 12) and the pCLuc-Basic2 vector as a template and then digesting the PCR-amplified product with NdeI and XbaI were inserted into the restriction site of a DNA fragment (6049 bp), which was obtained by digesting the pCBIN-CLUC vector with BamHI and XbaI, so as to prepare a pCBIN-CLUC4 vector (refer to FIG. 5).

The primers used are as follows.

❋ oSP4-f
(SEQ ID NO: 19)
5'-tt GGATCC gcc acc atg ggc tgg agc ctg-3'

❋ oSP4-r
(SEQ ID NO: 20)
5'-ttC ATA TGg aca gtc ctg gga cag cac cct ggt -3'

3-6: Preparation of pCBIN-CLUC5

A DNA fragment (74 bp), which was obtained via PCR amplification using two primers of SEQ ID NOS: 21 and 22 and a pSEAP-Basic2 vector, which is a reporter vector using secretory alkaline phosphatase (SEAP), as a template and then digesting the PCR-amplified product with BamHI and NdeI, and a DNA fragment (1654 bp), which was obtained via PCR amplification of a CLUC gene using two primers (SEQ ID NOS: 11 and 12) and the pCLuc-Basic2 vector as a template and then digesting the PCR-amplified product with NdeI and XbaI were inserted into the restriction site of a DNA fragment (6049 bp), which was obtained by digesting the pCBIN-CLUC vector with BamHI and XbaI, so as to prepare a pCBIN-CLUC5 vector (refer to FIG. 5).

The primers used are as follows.

❋ oSP5-f
(SEQ ID NO: 21)
5'-tt GGATCC gcc acc atg ctg ctg ctg ctg ctg ctg g-3'

❋ oSP5-r
(SEQ ID NO: 22)
5'-ttC ATA TGg aca gtc ctg gcc cag gga gag ctg-3'

3-7: Preparation of pCBIN-CLUC7.2

Figure 7:
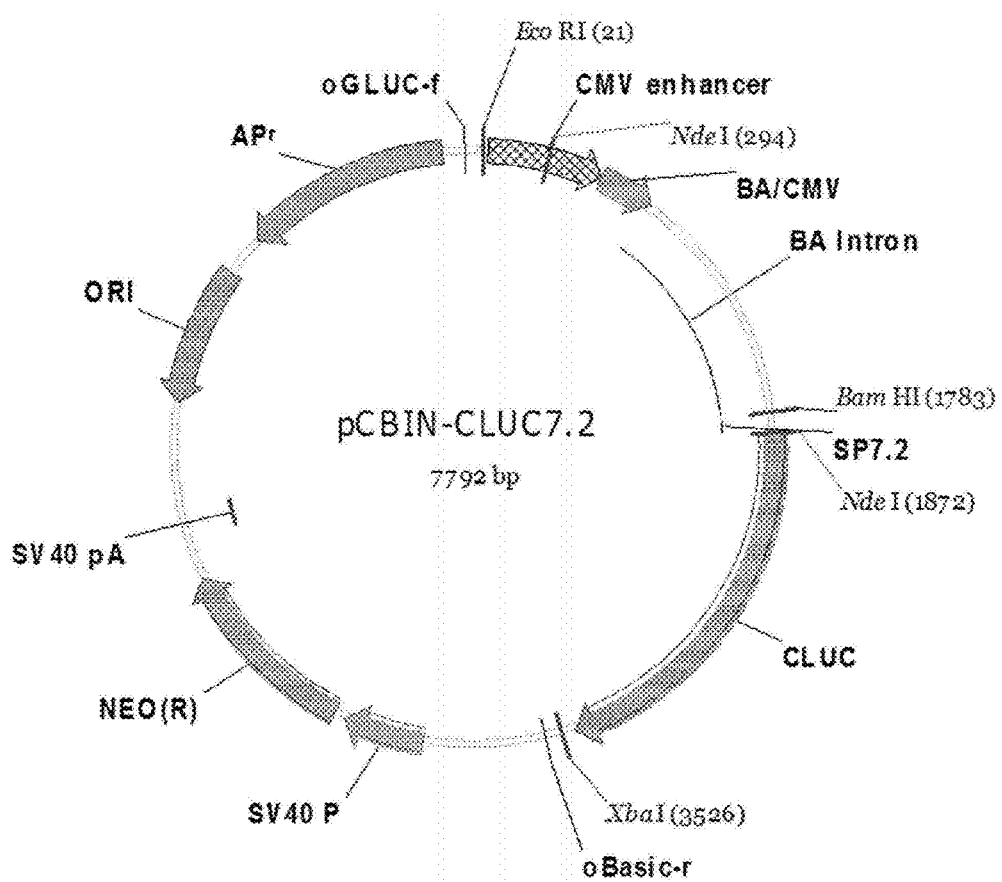
FIG. 7 shows a plasmid map of a luciferase expression vector pCBIN-CLUC7.2 having a protein secretion factor SP7.2 prepared by the present inventors.

A DNA fragment (89 bp) obtained via PCR amplification using two primers of SEQ ID NOS: 23 and 24 and pLFG250 (Korean Patent Application Publication No. 10-0954322), which has a LBFL313 gene, as a template and then digesting the PCR-amplified product with BamHI and NdeI, and a DNA fragment (1654 bp), which was obtained via PCR amplification a CLUC gene using two primers (SEQ ID NOS: 11 and 12) and the pCLuc-Basic2 vector as a template and then digesting the PCR-amplified product with NdeI and XbaI were inserted into the restriction site of a DNA fragment (6049 bp), which was obtained by digesting the pCBIN-CLUC vector with BamHI and XbaI, so as to prepare a pCBIN-CLUC7.2 vector (refer to FIG. 7).

The primers used are as follows.

❋ oSP7-B1-f2
(SEQ ID NO: 23)
5'-tt GGATCC gcc acc atg cac cgg cca gag-3'

❋ oSP7-N1-r
(SEQ ID NO: 24)
5'-ttC ATA TGg aca gtc ctg tgc cca ggt ggg gcc-3'

3-8: Preparation of pCBIN-CLUC7.3

Figure 8:
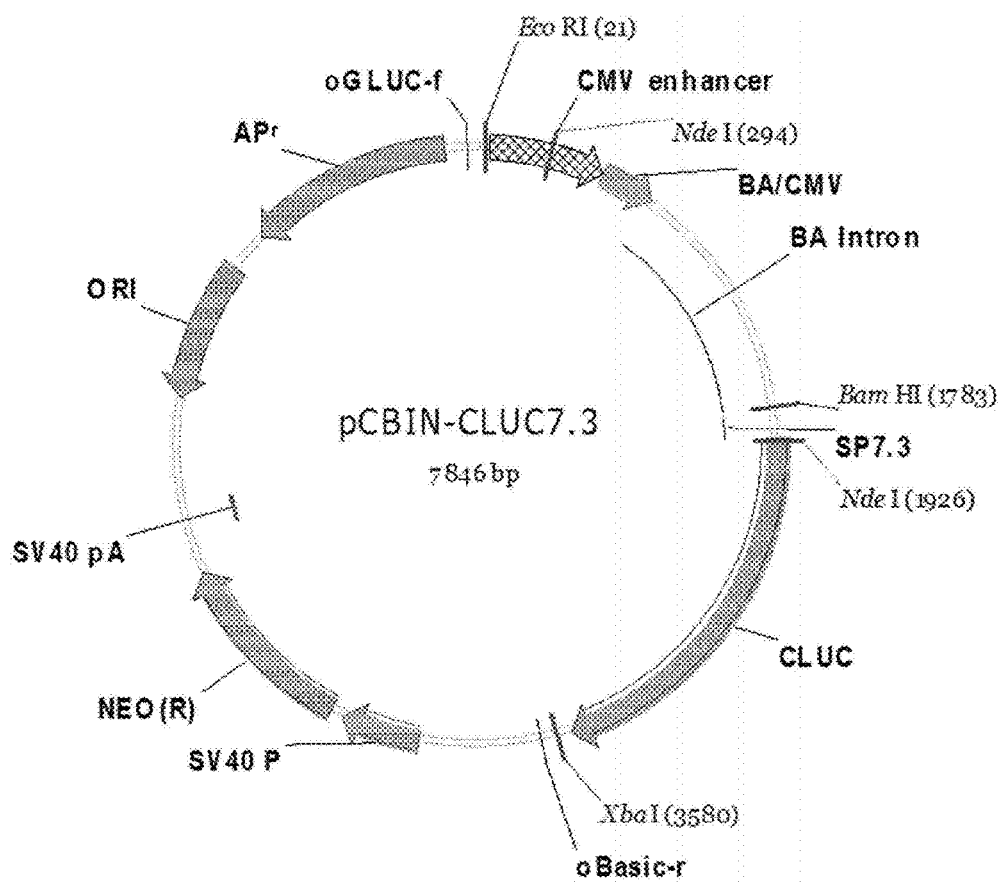
FIG. 8 shows a plasmid map of a luciferase expression vector pCBIN-CLUC7.3 having a protein secretion factor SP7.3 prepared by the present inventors.

A DNA fragment (143 bp), which was obtained via PCR amplification using two primers of SEQ ID NOS: 24 and 25 and pLFG250 (Korean Patent No. 10-0954322), which has a LBFL313 gene, as a template and then digesting the PCR-amplified product with BamHI and NdeI, and a DNA fragment (1654 bp), which was obtained via PCR amplification a CLUC gene using two primers (SEQ ID NOS: 11 and 12) and the pCLuc-Basic2 vector as a template and then digesting the PCR-amplified product with NdeI and XbaI were inserted into the cleft site of a DNA fragment (6049 bp), which was obtained by digesting the pCBIN-CLUC vector with BamHI and XbaI, so as to prepare a pCBIN-CLUC7.3 vector (refer to FIG. 8).

The used primer is as follows.
❋ oSP7-B1-f3 (SEQ ID NO: 25)
5'-tt GGATCC gcc acc atg tgg agg gtg ccc-3'

Example 4: In Vitro Secretion Efficacy Test of Luciferase Plasmid Vectors

Each of the luciferase plasmid vectors prepared in Example 3 is configured such that a secretory luciferase derived from *Cypridina noctiluca* is inserted as a reporter. In order to examine the extracellular secretion efficacy of a signal sequence in an in vitro cell culture system, the signal sequence was transformed in a CHO cell, and then the secretion inducing level of the signal sequence was examined through luciferase assay.

Specifically, each of the luciferase plasmid vectors prepared in Example 3 was transformed in a CHO cell, which was cultured in a Dulbecco's modified Eagle's medium (DMEM, manufactured by GIBCO-BRL Corporation) containing 10% of heat-inactivated fetal bovine serum (FBS, manufactured by GIBCO-BRL Corporation), using Lipofectamine™ 2000 (Invitrogen, Cat.#:11668-019). One day before the transformation, 6×10⁴ CHO cells per each well of a 24-well plate (Falcon Corporation) were cultured, and, on the next day, tube 1 (1 well reaction amount) filled with 500 ng of eight different types plasmid vectors (pCBIN-CLUC1, pCBIN-CLUC2, pCBIN-CLUC4, pCBIN-CLUC5, pCBIN-CLUC, pCBIN-CLUC7.2, and pCBIN-CLUC7.3), in each of which a luciferase gene is inserted, and 50 μL of Opti-MEM®I (invitrogen, Cat.#31985-070), and tube 2 (1 well reaction amount), filled with 2 μL of Lipofectamine™ 2000 and 48 μL of Opti-MEM®I, were respectively left at room temperature for 5 minutes, and then the two tubes were mixed to react at room temperature for 20 minutes. The mixture was added to the CHO cells in 250 μL of Opti-MEM®I in a volume of 100 μL and cultured in an incubator (5% $CO_2$) at 37° C., and then the DMEM containing 20% FBS was put into each well and cultured for 6 days. On the 2nd, 3rd, 5th, and 6th day after the transformation, the culture medium of each well was collected as a sample in the amount of 100 μL, stored at 20° C., completely dissolved, and on the 6th day, 20 μL each of the resultant was transferred into an assay plate, respectively, and subjected to luciferase assay.

As a result of the measurement of the luciferase secretion efficacy, as shown in FIG. 9, the secretion level of luciferase was improved in the total four signal sequences (SP2, SP6, SP7.2, and SP7.3) of the two signal sequences derived from a LBFL313 and the existing two signal sequences compared to the existing signal sequence (SP1). Particularly, it was confirmed that, in the case of SP7.2 and SP7.3 vectors, a large amount of luciferase is secreted at the early stage of culture (2d and 3d).

Examples 5: Preparation of Antibody Expression Plasmid Vectors

The following various antibody expression vectors were prepared by selecting SP2, SP6 and SP7.2 from among the signal sequences exhibiting effects in Example 4 in order to examine whether each of the prepared antibody expression vectors exhibits excellent secretion inducing ability even to a monoclonal antibody, for which an industrial large-scale production is required.

5-1: Preparation of pCB-Rx11_v5.4

Figure 10:
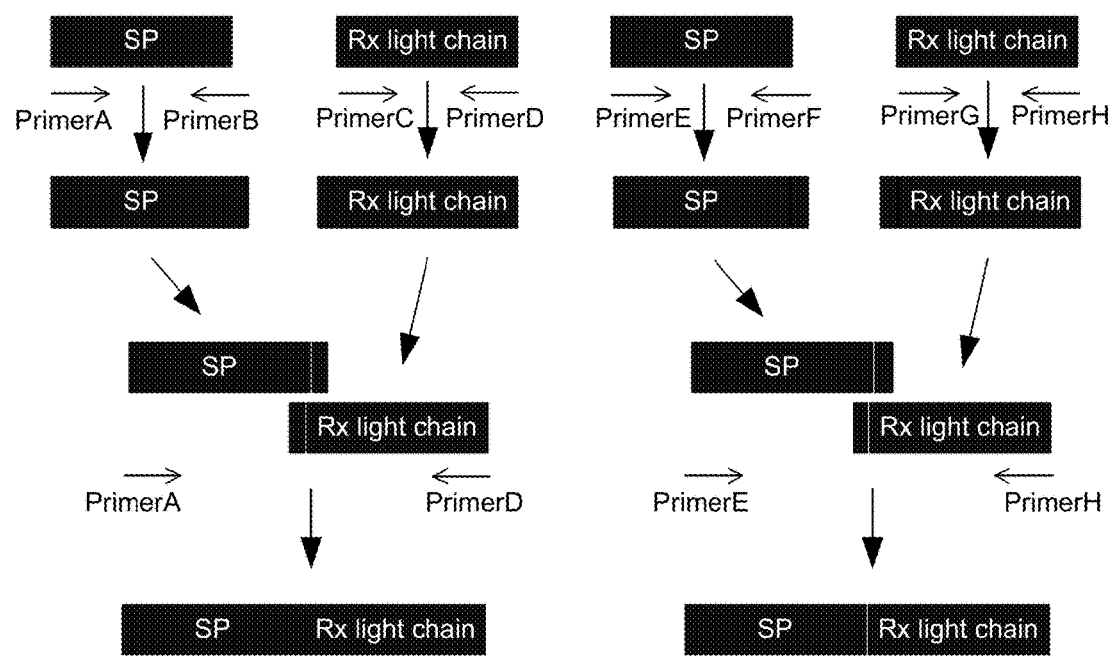
FIG. 10 is a schematic view showing a process of operably linking a protein secretion factor (SP) to light-chain and heavy-chain genes of an IgG1-type monoclonal antibody (Rx antibody) via in-frame.
Figure 11:
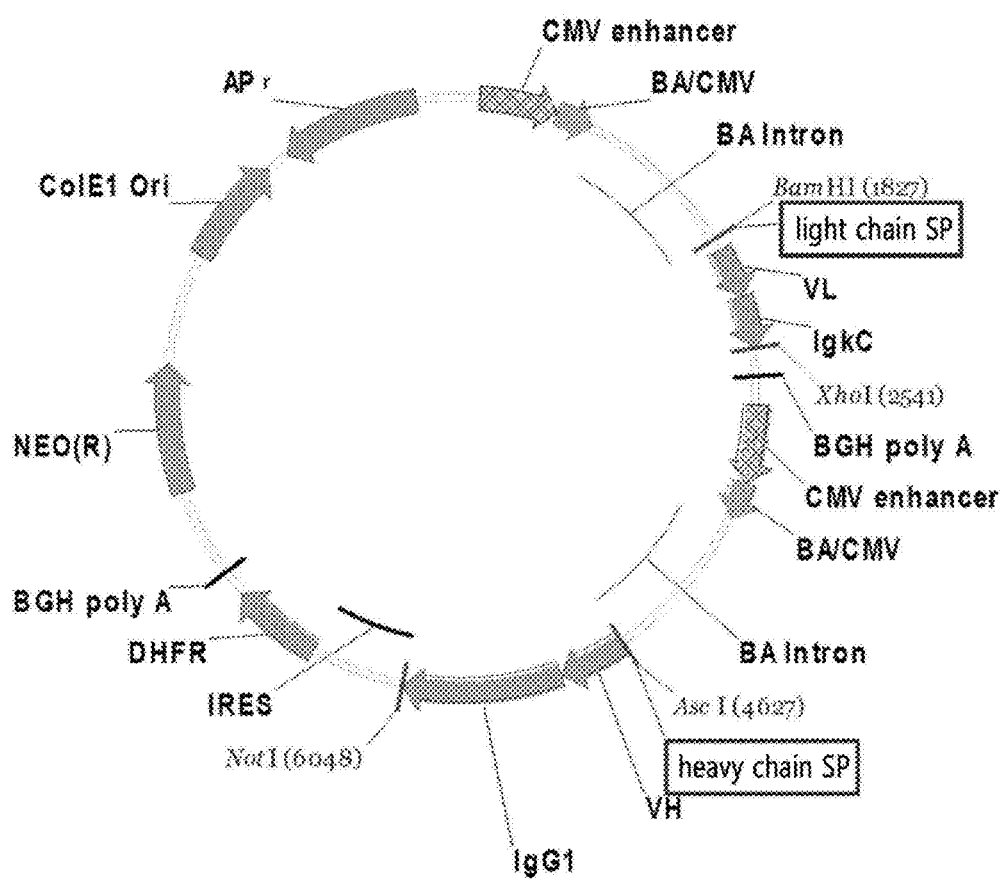
FIG. 11 is a plasmid map showing the general form of a pCB-Rx_v5.4 plasmid prepared by linking each protein secretion factor to light-chain and heavy-chain genes of an Rx antibody. In the present invention, the pCB-Rx_v5.4-based plasmids were prepared such that only the protein secretion factors inserted in the light chain SP and heavy chain SP of the plasmid map are different, and other portions of the plasmid map are identical.

A DNA fragment, which was obtained by digesting with BamHI and XhoI of a PCR product, in which SP1 and an antibody light chain are linked, obtained via PCR using four primers (SEQ ID NOS: 9, 26, 27, and 28) and the pCBIN-CLUC1 vector and pCB-Rx_v5.4 vector as templates, and a DNA fragment (refer to FIG. 10 and Table 2), which was obtained by digesting with AscI and NotI of a PCR product, in which SP1 and an antibody heavy chain are linked, obtained via PCR using four primers (SEQ ID NOS: 29, 30, 31, and 32) and the pCBIN-CLUC1 vector and pCB-Rx_v5.4 vector as templates, were inserted into the BamHI and XhoI sites of pCB-Rx_v5.4 and the AscI and NotI sites of pCB-Rx_v5.4, respectively, so as to prepare a pCB-Rx11_v5.4 vector (refer to FIG. 11 and Table 3).

The primers used are as follows.

✗ oIxLs-r1
(SEQ ID NO: 26)
5'-cag cag gat gtc gcc cct gga cat gat cac -3'

✗ oRx-LF1
(SEQ ID NO: 27)
5'-cag atc gtg ctg tct cag tct-3'

✗ oIkC-M1X1-r
(SEQ ID NO: 28)
5'-tt ACGCGT CTCGAG tca aca ctc tcc c-3'

✗ oRHn-f
(SEQ ID NO: 29)
5'-tt GGCGCGCC atg gga tgg agc tat-3'

✗ oIxLs-r2
(SEQ ID NO: 30)
5'-cag cag gat gtc gga cag cac cct ggt ggc cac ggc-3'

✗ oRx_HF1
(SEQ ID NO: 31)
5'-cag gtg cag ctg cag cag ccc-3'

✗ oIgG1-X1N1-r
(SEQ ID NO: 32)
5'-aa CTCGAG GCGGCCGC tca ttt acc cgg aga c-3'

TABLE 2

| Primer | SEQ ID NO: |
|---|---|
| A | 9 |
| B | 26 |
| C | 27 |
| D | 28 |
| E | 29 |
| F | 30 |
| G | 31 |
| H | 32 |

TABLE 3

| Plasmid | Type of light chain (SP) | Type of heavy chain (SP) |
|---|---|---|
| pCB-Rx11_v5.4 | SP1 | SP1 |

5-2: Preparation of pCB-Rx12_v5.4

A DNA fragment, which was obtained by digesting with BamHI and XhoI of a PCR product, in which SP1 and an antibody light chain are linked, obtained via PCR amplification using four primers (SEQ ID NOS: 9, 26, 27, and 28) and the pCBIN-CLUC1 vector and pCB-Rx_v5.4 vector as templates, and a DNA fragment (refer to FIG. 10 and Table 4), which was obtained by digesting with AscI and NotI of a PCR product, in which SP2 and an antibody heavy chain are linked, obtained via PCR amplification using four primers (SEQ ID NOS: 33, 34, 35, and 32) and the pCBIN-CLUC2 vector and pCB-Rx_v5.4 vector as templates, were inserted into the BamHI and XhoI sites of pCB-Rx_v5.4 and the AscI and NotI sites of pCB-Rx_v5.4, respectively, so as to prepare a pCB-Rx12_v5.4 vector (refer to FIG. 11 and Table 5).

The primers used are as follows.

✗ oAscI_SP2-f
(SEQ ID NO: 33)
5'-ctg gcg cgc cat gaa gtg ggt gac c-3'

-continued

✕ oSP2_RH-r
(SEQ ID NO: 34)
5'-gca gct gca cct gcc tcc tga aca c-3'

✕ oSP2_RH-f
(SEQ ID NO: 35)
5'-ctg ttc att gcc agg tgc agc tgc-3'

TABLE 4

| Primer | SEQ ID NO: |
|---|---|
| A | 9 |
| B | 26 |
| C | 27 |
| D | 28 |
| E | 33 |
| F | 34 |
| G | 35 |
| H | 32 |

TABLE 5

| Plasmid | Type of light chain (SP) | Type of heavy chain (SP) |
|---|---|---|
| pCB-Rx12_v5.4 | SP1 | SP2 |

5-3: Preparation of pCB-Rx16_v5.4

A DNA fragment, which was obtained by digesting with BamHI and XhoI of a PCR product, in which SP1 and an antibody light chain are linked, obtained via PCR amplification using four primers (SEQ ID NOS: 9, 26, 27, and 28) using the pCBIN-CLUC1 vector and pCB-Rx_v5.4 vector as templates, and a DNA fragment (refer to FIG. 10 and Table 6), which was obtained by digesting with AscI and NotI of a PCR product, in which SP6 and an antibody heavy chain are linked, obtained via PCR amplification using four primers (SEQ ID NOS: 36, 37, 38, and 32) and the pCBIN-CLUC3 vector and pCB-Rx_v5.4 vector as templates, were inserted into the BamHI and XhoI sites of pCB-Rx_v5.4 and the AscI and NotI sites of pCB-Rx_v5.4, respectively, so as to prepare a pCB-Rx16_v5.4 vector (refer to FIG. 11 and Table 7).

The primers used are as follows.

✕ oAscI_SP6-f
(SEQ ID NO: 36)
5'-CAG GCG CGC CAT GAA GAC CTT AAT TC-3'

✕ oSP6_RH-r
(SEQ ID NO: 37)
5'-GCA GCT GCA CCT GGC AAT GAA CAG-3'

✕ oSP6_RH-f
(SEQ ID NO: 38)
5'-CTG TTC ATT GCC AGG TGC AGC TGC-3'

TABLE 6

| Primer | SEQ ID NO |
|---|---|
| A | 9 |
| B | 26 |
| C | 27 |
| D | 28 |
| E | 36 |
| F | 37 |
| G | 38 |
| H | 32 |

TABLE 7

| Plasmid | Type of light chain (SP) | Type of heavy chain (SP) |
|---|---|---|
| pCB-Rx16_v5.4 | SP1 | SP6 |

5-4: Preparation of pCB-Rx17_v5.4

A DNA fragment, which was obtained by digesting with BamHI and XhoI of a PCR product, in which SP1 and an antibody light chain are linked, obtained via PCR amplification using four primers (SEQ ID NOS: 9, 26, 27, and 28) and the pCBIN-CLUC1 vector and pCB-Rx_v5.4 vector as templates, and a DNA fragment (refer to FIG. 10 and Table 8), which was obtained by digesting with AscI and NotI of a PCR product, in which SP7.2 and an antibody heavy chain are linked, obtained via PCR amplification using four primers via PCR amplification using four primers (SEQ ID NOS: 39, 40, 41, and 32) and the pCBIN-CLUC7.2 vector and pCB-Rx_v5.4 vector as templates, were inserted into the BamHI and XhoI sites of pCB-Rx_v5.4 and the AscI and NotI sites of pCB-Rx_v5.4, respectively, so as to prepare a pCB-Rx17_v5.4 vector (refer to FIG. 11 and Table 9).

The primers used are as follows.

✕ oAscI_SP7.2-f
(SEQ ID NO: 39)
5'-cag gcg cgc cat gca ccg gcc aga g-3'

✕ oSP7.2_RH-r
(SEQ ID NO: 40)
5'-gca gct gca cct gtg ccc agg tgg g-3'

✕ oSP7.2_RH-f
(SEQ ID NO: 41)
5'-ccc acc tgg gca cag gtg cag ctg c-3'

TABLE 8

| Primer | SEQ ID NO: |
|---|---|
| A | 9 |
| B | 26 |
| C | 27 |
| D | 28 |
| E | 39 |
| F | 40 |
| G | 41 |
| H | 32 |

TABLE 9

| Plasmid | Type of light chain (SP) | Type of heavy chain (SP) |
|---|---|---|
| pCB-Rx17_v5.4 | SP1 | SP7.2 |

5-5: Preparation of pCB-Rx21_v5.4

A DNA fragment, which was obtained by digesting with BamHI and XhoI of a PCR product, in which SP2 and an antibody light chain are linked, obtained via PCR amplification using four primers (SEQ ID NOS: 15, 42, 43, and 28) and the pCBIN-CLUC2 vector and pCB-Rx_v5.4 vector as templates, and a DNA fragment (refer to FIG. 10 and Table 10), which was obtained by digesting with AscI and NotI of a PCR product, in which SP1 and an antibody heavy chain are linked, obtained via PCR amplification using four primers s (SEQ ID NOS: 39, 40, 41, and 32) and the pCBIN-CLUC1 vector and pCB-Rx_v5.4 vector as templates, were inserted into the BamHI and XhoI sites of pCB-Rx_v5.4 and the AscI and NotI sites of pCB-Rx_v5.4, respectively, so as to prepare a pCB-Rx21_v5.4 vector (refer to FIG. 10 and Table 11).

The primers used are as follows.

※ oSP7.2_RH-r
(SEQ ID NO: 42)
5'-gca gct gca cct gtg ccc agg tgg g-3'

※ oSP7.2_RH-f
(SEQ ID NO: 43)
5'-ccc acc tgg gca cag gtg cag ctg c-3'

TABLE 10

| Primer | SEQ ID NO: |
|---|---|
| A | 9 |
| B | 42 |
| C | 43 |
| D | 28 |
| E | 39 |
| F | 40 |
| G | 41 |
| H | 32 |

TABLE 11

| Plasmid | Type of light chain (SP) | Type of heavy chain (SP) |
|---|---|---|
| pCB-Rx21_v5.4 | SP2 | SP1 |

5-6: Preparation of pCB-Rx22_v5.4

A DNA fragment, which was obtained by digesting with BamHI and XhoI of a PCR product, in which SP2 and an antibody light chain are linked, obtained via PCR amplification using four primers (SEQ ID NOS: 15, 42, 4, and 28) and the pCBIN-CLUC2 vector and pCB-Rx_v5.4 vector as templates, and a DNA fragment (refer to FIG. 10 and Table 12), which was obtained by digesting with AscI and NotI of a PCR product, in which SP2 and an antibody heavy chain are linked, obtained via PCR amplification using four primers (SEQ ID NOS: 33, 34, 35, and 32) and the pCBIN-CLUC2 vector and pCB-Rx_v5.4 vector as templates, were inserted into the BamHI and XhoI sites of pCB-Rx_v5.4 and the AscI and NotI sites of pCB-Rx_v5.4, respectively, so as to prepare a pCB-Rx22_v5.4 vector (refer to FIG. 10 and Table 13).

TABLE 12

| Primer | SEQ ID NO: |
|---|---|
| A | 9 |
| B | 42 |
| C | 43 |

TABLE 12-continued

| Primer | SEQ ID NO: |
|---|---|
| D | 28 |
| E | 33 |
| F | 34 |
| G | 35 |
| H | 32 |

TABLE 13

| Plasmid | Type of light chain (SP) | Type of heavy chain (SP) |
|---|---|---|
| pCB-Rx22_v5.4 | SP2 | SP2 |

5-7: Preparation of pCB-Rx26_v5.4

A DNA fragment, which was obtained by digesting with BamHI and XhoI of a PCR product, in which SP2 and an antibody light chain are linked, obtained via PCR amplification using four primers (SEQ ID NOS: 15, 42, 43, and 28) and the pCBIN-CLUC2 vector and pCB-Rx_v5.4 vector as templates, and a DNA fragment (refer to FIG. 10 and Table 14), which was obtained by digesting with AscI and NotI of a PCR product, in which SP6 and an antibody heavy chain are linked, obtained via PCR amplification using four primerss (SEQ ID NOS: 36, 37, 38, and 32) and the pCBIN-CLUC vector and pCB-Rx_v5.4 vector as templates, were inserted into the BamHI and XhoI sites of pCB-Rx_v5.4 and the AscI and NotI sites of pCB-Rx_v5.4, respectively, so as to prepare a pCB-Rx26_v5.4 vector (refer to FIG. 11 and Table 15).

TABLE 14

| Primer | SEQ ID NO: |
|---|---|
| A | 15 |
| B | 42 |
| C | 43 |
| D | 28 |
| E | 36 |
| F | 37 |
| G | 38 |
| H | 32 |

TABLE 15

| Plasmid | Type of light chain (SP) | Type of heavy chain (SP) |
|---|---|---|
| pCB-Rx26_v5.4 | SP2 | SP6 |

5-8: Preparation of pCB-Rx27_v5.4

A DNA fragment, which was obtained by digesting with BamHI and XhoI of a PCR product, in which SP2 and an antibody light chain are linked, obtained via PCR amplification using four primerss (SEQ ID NOS: 15, 42, 43, and 28) and the pCBIN-CLUC2 vector and pCB-Rx_v5.4 vector as templates, and a DNA fragment (refer to FIG. 10 and Table 16), which was obtained by digesting with AscI and NotI of a PCR product, in which SP6 and an antibody heavy chain are linked, obtained via PCR amplification using four primers via PCR amplification using four primers (SEQ ID NOS: 39, 40, 41, and 32) and the pCBIN-CLUC7.2 vector and pCB-Rx_v5.4 vector as templates, were inserted into the BamHI and XhoI sites of pCB-Rx_v5.4 and the AscI and NotI sites of pCB-Rx_v5.4, respectively, so as to prepare a pCB-Rx27_v5.4 vector (refer to FIG. 11 and Table 17).

TABLE 16

| Primer | SEQ ID NO: |
|---|---|
| A | 15 |
| B | 42 |
| C | 43 |
| D | 28 |
| E | 39 |
| F | 40 |
| G | 41 |
| H | 32 |

TABLE 17

| Plasmid | Type of light chain (SP) | Type of heavy chain (SP) |
|---|---|---|
| pCB-Rx27_v5.4 | SP2 | SP7.2 |

5-9: Preparation of pCB-Rx32_v5.4

A DNA fragment (refer to FIG. 10 and Table 18), which was obtained by digesting with AscI and NotI of a PCR product, in which SP2 and an antibody heavy chain are linked, obtained via PCR amplification using four primers (SEQ ID NOS: 33, 34, 35, and 32) and the pCBIN-CLUC2 vector and pCB-Rx_v5.4 vector as templates, was inserted into the AscI and NotI sites of pCB-Rx_v5.4, so as to prepare a pCB-Rx32_v5.4 vector (refer to FIG. 11 and Table 19).

TABLE 18

| Primer | SEQ ID NO: |
|---|---|
| E | 33 |
| F | 34 |
| G | 35 |
| H | 32 |

TABLE 19

| Plasmid | Type of light chain (SP) | Type of heavy chain (SP) |
|---|---|---|
| pCB-Rx32_v5.4 | SP3 | SP2 |

5-10: Preparation of pCB-Rx36_v5.4

A DNA fragment (refer to FIG. 10 and Table 20), which was obtained by digesting with AscI and NotI of a PCR product, in which SP6 and an antibody heavy chain are linked, obtained via PCR amplification using four primers (SEQ ID NOS: 36, 37, 38, and 32) and the pCBIN-CLUC vector and pCB-Rx_v5.4 vector as templates, was inserted into the AscI and NotI sites of pCB-Rx_v5.4, so as to prepare a pCB-Rx36_v5.4 vector (refer to FIG. 11 and Table 21).

TABLE 20

| Primer | SEQ ID NO: |
|---|---|
| E | 36 |
| F | 37 |
| G | 38 |
| H | 32 |

TABLE 21

| Plasmid | Type of light chain (SP) | Type of heavy chain (SP) |
|---|---|---|
| pCB-Rx36_v5.4 | SP3 | SP6 |

5-11: Preparation of pCB-Rx37_v5.4

A DNA fragment (refer to FIG. 10 and Table 22), which was obtained by digesting with AscI and NotI of a PCR product, in which SP7.2 and an antibody heavy chain are linked, obtained via PCR amplification using four primers (SEQ ID NOS: 39, 40, 41, and 32) and the pCBIN-CLUC7.2 vector and pCB-Rx_v5.4 vector as templatess, was inserted into the AscI and NotI sites of pCB-Rx_v5.4, so as to prepare a pCB-Rx37_v5.4 vector (refer to FIG. 11 and Table 23).

TABLE 22

| Primer | SEQ ID NO: |
|---|---|
| E | 39 |
| F | 40 |
| G | 41 |
| H | 32 |

TABLE 23

| Plasmid | Type of light chain (SP) | Type of heavy chain (SP) |
|---|---|---|
| pCB-Rx37_v5.4 | SP3 | SP7.2 |

5-12: Preparation of pCB-Rx61_v5.4

A DNA fragment, which was obtained by digesting with BamHI and XhoI of a PCR product, in which SP6 and an antibody light chain are linked, obtained via PCR amplification using four primers (SEQ ID NOS: 44, 45, 46, and 28) and the pCBIN-CLUC vector and pCB-Rx_v5.4 vector as templates, and a DNA fragment (refer to FIG. 10 and Table 24), which was obtained by digesting with AscI and NotI of a PCR product, in which SP1 and an antibody heavy chain are linked, obtained via PCR amplification using four primers (SEQ ID NOS: 29, 30, 31, and 32) and the pCBIN-CLUC1 vector and pCB-Rx_v5.4 vector as templates, were inserted into the BamHI and XhoI sites of pCB-Rx_v5.4 using BamHI and XhoI and the AscI and NotI sites of pCB-Rx_v5.4, respectively, so as to prepare a pCB-Rx61_v5.4 vector (refer to FIG. 11 and Table 25).

TABLE 24

| Primer | SEQ ID NO: |
|---|---|
| A | 44 |
| B | 45 |
| C | 46 |

TABLE 24-continued

| Primer | SEQ ID NO: |
| --- | --- |
| D | 28 |
| E | 29 |
| F | 30 |
| G | 31 |
| H | 32 |

TABLE 25

| Plasmid | Type of light chain (SP) | Type of heavy chain (SP) |
| --- | --- | --- |
| pCB-Rx61_v5.4 | SP6 | SP1 |

The primers used are as follows.

※ oSP6-f
(SEQ ID NO: 44)
5'-tt GGATCC gcc acc atg aag acc tta att-3'

※ oSP6_RL-r
(SEQ ID NO: 45)
5'-ACA GCA CGA TCT GGC AAT GAA CAG-3'

※ oSP6_RL-f
(SEQ ID NO: 46)
5'-CTG TTC ATT GCC AGA TCG TGC TGT-3'

5-13: Preparation of pCB-Rx62_v5.4

A DNA fragment, which was obtained by digesting with BamHI and XhoI of a PCR product, in which SP6 and an antibody light chain are linked, obtained via PCR amplification using four primers via PCR amplification using (SEQ ID NOS: 44, 45, 46, and 28) and the pCBIN-CLUC vector and pCB-Rx_v5.4 vector as templates, and a DNA fragment (refer to FIG. 10 and Table 26), which was obtained by digesting with AscI and NotI of a PCR product, in which SP2 and an antibody heavy chain are linked, obtained via PCR amplification using four primers via PCR amplification using (SEQ ID NOS: 33, 34, 35 and 32) and the pCBIN-CLUC2 vector and pCB-Rx_v5.4 vector as templates, were inserted into the BamHI and XhoI sites of pCB-Rx_v5.4 and the AscI and NotI sites of pCB-Rx_v5.4, respectively, so as to prepare a pCB-Rx62_v5.4 vector (refer to FIG. 11 and Table 27).

TABLE 26

| Primer | SEQ ID NO: |
| --- | --- |
| A | 44 |
| B | 45 |
| C | 46 |
| D | 28 |
| E | 33 |
| F | 34 |
| G | 35 |
| H | 32 |

TABLE 27

| Plasmid | Type of light chain (SP) | Type of heavy chain (SP) |
| --- | --- | --- |
| pCB-Rx62_v5.4 | SP6 | SP2 |

5-14: Preparation of pCB-Rx66_v5.4

A DNA fragment, which was obtained by digesting with BamHI and XhoI of a PCR product, in which SP6 and an antibody light chain are linked, obtained via PCR amplification using four primers via PCR amplification using (SEQ ID NOS: 44, 45, 46, and 28) and the pCBIN-CLUC vector and pCB-Rx_v5.4 vector as templates, and a DNA fragment (refer to FIG. 10 and Table 28), which was obtained by digesting with AscI and NotI of a PCR product, in which SP6 and an antibody heavy chain are linked, obtained via PCR amplification using four primers via PCR amplification using (SEQ ID NOS: 36, 37, 38, and 32) and the pCBIN-CLUC vector and pCB-Rx_v5.4 vector as templates, were inserted into the BamHI and XhoI sites of pCB-Rx_v5.4 using BamHI and XhoI and the AscI and NotI sites of pCB-Rx_v5.4, respectively, so as to prepare a pCB-Rx66_v5.4 vector (refer to FIG. 11 and Table 29).

TABLE 28

| Primer | SEQ ID NO: |
| --- | --- |
| A | 44 |
| B | 45 |
| C | 46 |
| D | 28 |
| E | 36 |
| F | 37 |
| G | 38 |
| H | 32 |

TABLE 29

| Plasmid | Type of light chain (SP) | Type of heavy chain (SP) |
| --- | --- | --- |
| pCB-Rx66_v5.4 | SP6 | SP6 |

5-15: Preparation of pCB-Rx67_v5.4

A DNA fragment, which was obtained by digesting with BamHI and XhoI of a PCR product, in which SP6 and an antibody light chain are linked, obtained via PCR amplification using four primers via PCR amplification using four primers (SEQ ID NOS: 44, 45, 46, and 28) and the pCBIN-CLUC vector and pCB-Rx_v5.4 vector as templates, and a DNA fragment (refer to FIG. 10 and Table 30), which was obtained by digesting with AscI and NotI of a PCR product, in which SP7.2 and an antibody heavy chain are linked, obtained via PCR amplification using four primers via PCR amplification using (SEQ ID NOS: 39, 40, 41, and 32) and the pCBIN-CLUC7.2 vector and pCB-Rx_v5.4 vector as templates, were inserted into the BamHI and XhoI sites of pCB-Rx_v5.4 and the AscI and NotI sites of pCB-Rx_v5.4, respectively, so as to prepare a pCB-Rx67_v5.4 vector (refer to FIG. 11 and Table 31).

TABLE 30

| Primer | SEQ ID NO: |
| --- | --- |
| A | 44 |
| B | 45 |
| C | 46 |
| D | 28 |
| E | 39 |
| F | 40 |

TABLE 30-continued

| Primer | SEQ ID NO: |
|---|---|
| G | 41 |
| H | 32 |

TABLE 31

| Plasmid | Type of light chain (SP) | Type of heavy chain (SP) |
|---|---|---|
| pCB-Rx67_v5.4 | SP6 | SP7.2 |

5-16: Preparation of pCB-Rx71_v5.4

A DNA fragment, which was obtained by digesting with BamHI and XhoI of a PCR product, in which SP7.2 and an antibody light chain are linked, obtained via PCR amplification using four primers via PCR amplification using (SEQ ID NOS: 23, 42, 43, and 28) and the pCBIN-CLUC7.2 vector and pCB-Rx_v5.4 vector as templates, and a DNA fragment (refer to FIG. 10 and Table 32), which was obtained by digesting with AscI and NotI of a PCR product, in which SP1 and an antibody heavy chain are linked, obtained via PCR amplification using four primers via PCR amplification using (SEQ ID NOS: 29, 30, 31, and 32) and the pCBIN-CLUC1 vector and pCB-Rx_v5.4 vector as templates, were inserted into the BamHI and XhoI sites of pCB-Rx_v5.4 using BamHI and XhoI and the AscI and NotI sites of pCB-Rx_v5.4, respectively, so as to prepare a pCB-Rx71_v5.4 vector (refer to FIG. 11 and Table 33).

TABLE 32

| Primer | SEQ ID NO: |
|---|---|
| A | 23 |
| B | 42 |
| C | 43 |
| D | 28 |
| E | 29 |
| F | 30 |
| G | 31 |
| H | 32 |

TABLE 33

| Plasmid | Type of light chain (SP) | Type of heavy chain (SP) |
|---|---|---|
| pCB-Rx71_v5.4 | SP7.2 | SP1 |

5-17: Preparation of pCB-Rx72_v5.4

A DNA fragment, which was obtained by digesting with BamHI and XhoI of a PCR product, in which SP7.2 and an antibody light chain are linked, obtained via PCR amplification using four primers via PCR amplification using (SEQ ID NOS: 23, 42, 43, and 28) and the pCBIN-CLUC7.2 vector and pCB-Rx_v5.4 vector as templates, and a DNA fragment (refer to FIG. 10 and Table 34), which was obtained by digesting with AscI and NotI of a PCR product, in which SP2 and an antibody heavy chain are linked, obtained via PCR amplification using four primers via PCR amplification using (SEQ ID NOS: 33, 34, 35, and 32) and the pCBIN-CLUC7.2 vector and pCB-Rx_v5.4 vector as templates, were inserted into the BamHI and XhoI sites of pCB-Rx_v5.4 and the AscI and NotI sites of pCB-Rx_v5.4, respectively, so as to prepare a pCB-Rx72_v5.4 vector (refer to FIG. 11 and Table 35).

TABLE 34

| Primer | SEQ ID NO: |
|---|---|
| A | 23 |
| B | 42 |
| C | 43 |
| D | 28 |
| E | 33 |
| F | 34 |
| G | 35 |
| H | 32 |

TABLE 35

| Plasmid | Type of light chain (SP) | Type of heavy chain (SP) |
|---|---|---|
| pCB-Rx72_v5.4 | SP7.2 | SP2 |

5-18: Preparation of pCB-Rx76_v5.4

A DNA fragment, which was obtained by digesting with BamHI and XhoI of a PCR product, in which SP7.2 and an antibody light chain are linked, obtained via PCR amplification using four primers via PCR amplification using (SEQ ID NOS: 23, 42, 43, and 28) and the pCBIN-CLUC7.2 vector and pCB-Rx_v5.4 vector as templates, and a DNA fragment (refer to FIG. 10 and Table 36), which was obtained by digesting with AscI and NotI of a PCR product, in which SP6 and an antibody heavy chain are linked, obtained via PCR amplification using four primers via PCR amplification using (SEQ ID NOS: 36, 37, 38, and 32) and the pCBIN-CLUC vector and pCB-Rx_v5.4 vector as templates, were inserted into the BamHI and XhoI sites of pCB-Rx_v5.4I and the AscI and NotI sites of pCB-Rx_v5.4, respectively, so as to prepare a pCB-Rx76_v5.4 vector (refer to FIG. 11 and Table 37).

TABLE 36

| Primer | SEQ ID NO: |
|---|---|
| A | 23 |
| B | 42 |
| C | 43 |
| D | 28 |
| E | 36 |
| F | 37 |
| G | 38 |
| H | 32 |

TABLE 37

| Plasmid | Type of light chain (SP) | Type of heavy chain (SP) |
|---|---|---|
| pCB-Rx76_v5.4 | SP7.2 | SP6 |

5-19: Preparation of pCB-Rx77_v5.4

A DNA fragment, which was obtained by digesting with BamHI and XhoI of a PCR product, in which SP7.2 and an antibody light chain are linked, obtained via PCR amplification using four primers via PCR amplification using (SEQ ID NOS: 23, 42, 43, and 28) and the pCBIN-CLUC7.2 vector and pCB-Rx_v5.4 vector as templates, and a DNA fragment (refer to FIG. 10 and Table 38), which was obtained by digesting with AscI and NotI of a PCR product, in which SP7.2 and an antibody heavy chain are linked, obtained via PCR amplification using four primers via PCR amplification using (SEQ ID NOS: 39, 40, 41, and 32) and the pCBIN-CLUC7.2 vector and pCB-Rx_v5.4 vector as templates, were inserted into the BamHI and XhoI sites of pCB-Rx_v5.4 and the AscI and NotI sites of pCB-Rx_v5.4, respectively, so as to prepare a pCB-Rx77_v5.4 vector (refer to FIG. 11 and Table 39).

TABLE 38

| Primer | SEQ ID NO: |
|---|---|
| A | 23 |
| B | 42 |
| C | 43 |
| D | 28 |
| E | 39 |
| F | 40 |
| G | 41 |
| H | 32 |

TABLE 39

| Plasmid | Type of light chain (SP) | Type of heavy chain (SP) |
|---|---|---|
| pCB-Rx77_v5.4 | SP7.2 | SP7.2 |

Example 6: In Vitro Secretion Efficacy Test of Antibody Expression Plasmid Vectors Each of the antibody expression plasmid vectors prepared in Example 5 is constructed such that a mouse-human chimeric IgG1 type monoclonal antibody is secreted to the outside of a cell. In order to examine the extracellular secretion efficacy of a signal sequence in an in vitro cell culture system, the monoclonal antibody was transformed in a CHO cell, and then the secretion level of the monoclonal antibody was examined via ELISA.

Specifically, each of the antibody expression plasmid vectors prepared in Example 5 was transformed into a CHO cell, which was cultured in a Dulbecco's modified Eagle's medium (DMEM, manufactured by GIBCO-BRL Corporation) containing 10% of heat-inactivated fetal bovine serum (FBS, manufactured by GIBCO-BRL Corporation), using Lipofectamine™ 2000 (Invitrogen, Cat.#:11668-019). One day before the transformation, $5 \times 10^6$ CHO cells per each dish were cultured using phi-100 dishes (Falcon Corporation), and on the next day, tube 1 (1 dish reaction amount) filled with 36 ng of 16 different types of plasmid vectors, in each of which was inserted with a luciferase gened, and 1.5 mL of Opti-MEM®I (invitrogen, Cat.#31985-070), and tube 2 (1 dish reaction amount) filled with 90 μL of Lipofectamine™ 2000 and 1410 μL of Opti-MEM®I, were respectively left at room temperature for 5 minutes, and then the two tubes were mixed to react at room temperature for 20 minutes. The mixture was added to the CHO cells in 5 mL of Opti-MEM®I in a volume of 3 mL and cultured in an incubator (5% $CO_2$) at 37° C. for 3 hours, and then the DMEM culture medium containing 20% FBS was put into each dish by 5 mL and cultured for 8 days. On the 2nd, 4th, 6th, and 8th day after the transformation, the culture medium in each dish was collected as a sample in a volume of 500 ul, respectively, stored at 20° C., and then all dissolved on the 8th day, transferred into an assay plate in a volume of 100 μL and subjected to ELISA assay.

The ELISA assay was performed at 4° C. using an O/N-coated 96-well plate and an anti-human Kappa Light chains-peroxidase (A7164-1 mL, sigma) under the condition that F(ab')$_2$ fragments of goat anti-human IgG and Fc gamma fragment specific (Pierce, 31163) were set to 0.2 ug/mL, respectively.

As a result of measurement of antibody secretion level via ELISA assay, as shown in FIG. 12, it was found that the secretion level of the expression vector pCB-Rx71_v5.4 including signal sequence SP7.2 encoding an amino acid sequence of SEQ ID NO: 1 derived from an LBFL313 gene was high. Particularly, it was found that the amount of secretion of a combination, in which signal sequence SP7.2 is linked to an antibody light chain and a signal sequence SP1 encoding an amino acid sequence of SEQ ID NO: 3 is linked to an antibody heavy chain, was significantly high, and that the amount of secretion thereof increased with the increase in culture time. Accordingly, it was found that, when signal sequence SP7.2 was used, the secretion level of the combination was very high even in a long-term culture compared to the result of the luciferase secretion test, in which the secretion level of luciferase was high in a short-term culture.

From the foregoing, those skilled in the art will appreciate that many variations and modifications can be made to the exemplary embodiments without substantially departing from the principles of the present invention. Therefore, the disclosed preferred embodiments of the invention are used in a generic and descriptive sense only and not for purposes of limitation.

The invention claimed is:

1. An expression cassette, comprising a promoter, which is operably linked to a nucleic acid sequence encoding a protein secretion factor having an amino acid sequence of SEQ ID NO: 2, which is operably linked to the gene encoding the target protein, wherein the protein secretion factor is not a natural signal sequence of the target protein.

2. A vector for secretory expression of target protein, comprising an expression cassette comprising a promoter, which is operably linked to a nucleic acid sequence encoding a protein secretion factor having an amino acid sequence of SEQ ID NO: 2, which is operably linked to a gene encoding a target protein, wherein the protein secretion factor is not a natural signal sequence of the target protein.

3. The vector according to claim 2, wherein the protein is selected from the group consisting of human growth hormones, serum proteins, antibodies, immunoglobulins, cytokines, α-, β- and γ-interferons, colony-stimulating factors (GM-CSF), platelet-derived growth factors (PDGF), phospholipase-activating protein (PLAP)s, insulins, tumor necrosis factors (TNF), growth factors, hormones, calcitonins, calcitonin gene related peptides (CGRP), enkephalins, somatomedins, erythropoietins, hypothalamic secretion factors, prolactins, chorionic gonadotropins, tissue plasminogen activators, growth hormone releasing peptides (GHRP), thymic humoral factors (THF), asparaginases, arginases, arginine deaminases, adenosine deaminases, peroxide dismutases, endotoxinase, catalases, chymotrypsins, lipases, uricases, adenosine diphosphatases, tyrosinases, bilirubin oxidases, glucose oxidases, glucosidases, galactosidases, glucocerebrosidases, and glucourodinases.

4. A method of producing a target protein, comprising:
   i) culturing a transformed cell, into which the vector according to claim 3 is introduced, to express a target protein and secrete the target protein to the outside of the cell; and
   ii) recovering the target protein from a culture or culture supernatant of the cell of step i).

5. A transformed cell, comprising the vector according to claim 2.

6. The transformed cell according to claim 5, wherein the cell is an animal cell.

7. A method of producing a target protein, comprising:
   i) culturing a transformed cell, into which the vector according to claim 2 is introduced, to express a target protein and secrete the target protein to the outside of the cell; and
   ii) recovering the target protein from a culture or culture supernatant of the cell of step i).

8. The method according to claim 7, further comprising purifying the recovered target protein.

9. The method according to claim 7, wherein the cell is a Chinese Hamster Ovary (CHO) cell.

10. A vector for secretory expression of an antibody, wherein the vector comprises:
    a) a first expression cassette comprising a promoter, which is operably linked to a nucleic acid sequence encoding a protein secretion factor having an amino acid sequence of SEQ ID NO: 1, which is operably linked to a gene encoding an antibody light chain; and
    b) a second expression cassette comprising a promoter is operably linked to a nucleic acid sequence encoding a protein secretion having an amino acid sequence of SEQ ID NO: 3, which is operably linked to a gene encoding an antibody heavy chain.

11. The vector according to claim 10, wherein the antibody light chain has an amino acid sequence of SEQ ID NO: 48, and the antibody heavy chain has an amino acid sequence of SEQ ID NO: 49.

12. A method of producing an antibody, comprising:
    i) culturing a transformed cell, into which the vector according to claim 10 is introduced, to express an antibody and secrete the antibody to the outside of the cell; and
    ii) recovering the antibody from a culture or culture supernatant of the cell of step i).

13. A transformed cell, comprising the vector according to claim 10.

14. The transformed cell according to claim 13, wherein the cell is an animal cell.

* * * * *